United States Patent
Bar-Or et al.

(10) Patent No.: US 10,533,986 B2
(45) Date of Patent: Jan. 14, 2020

(54) DETERMINATION OF FERTILITY POTENTIAL FROM THE OXIDATION-REDUCTION POTENTIAL OF A BIOLOGICAL SAMPLE

(71) Applicant: Aytu BioScience, Inc., Englewood, CO (US)

(72) Inventors: Raphael Bar-Or, Denver, CO (US); David Bar-Or, Englewood, CO (US); Leonard T. Rael, Centennial, CO (US); Kimberly B. Bjugstad, Lone Tree, CO (US); Ashok Agarwal, Moreland Hills, OH (US); Rakesh Sharma, Shaker Height, OH (US); Sajal Gupta, Cleveland Heights, OH (US)

(73) Assignee: Aytu BioScience, Inc., Englewood, CO (US)

( * ) Notice: Subject to any disclaimer, the term of this patent is extended or adjusted under 35 U.S.C. 154(b) by 0 days.

(21) Appl. No.: 16/112,158

(22) Filed: Aug. 24, 2018

(65) Prior Publication Data
US 2019/0154653 A1 May 23, 2019

Related U.S. Application Data

(63) Continuation of application No. 15/466,140, filed on Mar. 22, 2017, now Pat. No. 10,088,466, which is a continuation of application No. PCT/US2015/062455, filed on Nov. 24, 2015.

(60) Provisional application No. 62/084,414, filed on Nov. 25, 2014.

(51) Int. Cl.
| | | |
|---|---|---|
| G01N 33/487 | (2006.01) | |
| G01N 27/416 | (2006.01) | |
| A61B 10/00 | (2006.01) | |
| G16H 50/30 | (2018.01) | |
| G06F 19/00 | (2018.01) | |

(52) U.S. Cl.
CPC ... *G01N 33/48707* (2013.01); *A61B 10/0045* (2013.01); *A61B 10/0058* (2013.01); *G01N 27/4168* (2013.01); *G06F 19/00* (2013.01); *G16H 50/30* (2018.01); *A61B 2010/0074* (2013.01)

(58) Field of Classification Search
None
See application file for complete search history.

(56) References Cited

U.S. PATENT DOCUMENTS

| | | | |
|---|---|---|---|
| 5,290,519 | A | 3/1994 | Bar-Or et al. |
| 9,360,446 | B2 | 6/2016 | Bar-Or et al. |
| 9,410,913 | B2 | 8/2016 | Bar-Or et al. |
| 1,008,846 | A1 | 10/2018 | Bar-Or et al. |
| 2005/0142613 | A1 | 6/2005 | Bar-Or et al. |

FOREIGN PATENT DOCUMENTS

| | | |
|---|---|---|
| CA | 2203828 | 5/1996 |
| WO | WO 2014/066533 | 5/2014 |

OTHER PUBLICATIONS

Arafa et al. "Semen quality and infertility status can be identified through measures of oxidation-reduction potential," Andrologia, Mar. 2018, vol. 50, No. 2, e12881, 6 pages.
Bonde et al. "Relation between semen quality and fertility: a population-based study of 430 first-pregnancy planners," The Lancet, Oct. 1998, vol. 352, No. 9135, pp. 1172-1177.
Buck Louis et al. "Semen quality and time to pregnancy: the Longitudinal Investigation of Fertility and the Environment Study," Fertility and Sterility, Feb. 2014, vol. 101, No. 2, pp. 453-462.
Wang et al. "Limitations of semen analysis as a test of male fertility and anticipated needs from newer tests," Fertility and Sterility, Dec. 2014, vol. 102, No. 6, pp. 1502-1507.
Zinaman et al. "Semen quality and human fertility: a prospective study with healthy couples." Journal of Andrology, Jan.-Feb. 2000, vol. 21, No. 1, pp. 145-153.
English Translation of Official Action for China Patent Application No. 201580062907.3, dated Jun. 20, 2019 6 pages.
"RedoxSYS System User Manual," LUOXIS, 2015, 12 pages [retrieved online from: science.kyst.com.tw/upload/pdfs1505110918176286.pdf].
Abu et al. "Accurate sperm morphology assessment predicts sperm function," Andrologia, May 2012, vol. 44, Suppl 1, pp. 571-577.
Agarwal et al. "Role of oxidative stress in female reproduction," Reproductive Biology and Endocrinology, 2005, vol. 3:28, 21 pages.
Agarwal et al. "Mechanisms of oligozoospermia: an oxidative stress perspective," Systems Biology in Reproductive Medicine, 2014, vol. 60, pp. 206-216.
Agarwal et al. "Characterizing semen parameters and their association with reactive oxygen species in infertile men," Reproductive Biology and Endocrinology, 2014, vol. 12:33, 9 pages.
Agarwal et al. "Establishing the Oxidation-Reduction Potential in Semen and Seminal Plasma," Fertility and Sterility, Sep. 2015, vol. 104, No. 3, Supplement, abstract P-116, p. e146.

(Continued)

*Primary Examiner* — Robert J Yamasaki
(74) *Attorney, Agent, or Firm* — Sheridan Ross P.C.

(57) ABSTRACT

Methods and systems for measuring and using the oxidation-reduction potential (ORP) of a biological sample are provided. The system generally includes a test strip and a readout device for determining the ORP. The measured ORP is then used to determine characteristics relating to the fertility of the sample or the subject from which the sample was derived. Some characteristics that can be determined include the quality of a sperm sample, an oocyte or a fertilized egg. The measured ORP value can also be used to determine the specific characteristics of a spermatozoa sample, such as the morphology of the spermatozoa, the motility of the spermatozoa, the number of cells in the sample and the concentration of the cells in the sample. Knowledge of such characteristics and fertility potential can be used to identify individuals that might benefit from specific fertility treatments.

14 Claims, 19 Drawing Sheets

(56) References Cited

OTHER PUBLICATIONS

Agarwal et al. "Effect of Oxidative Stress on Male Reproduction," The World Journal of Men's Health, Apr. 2014, vol. 32, No. 1, 17 pages.
Auger "Assessing human sperm morphology: top models, underdogs or biometrics?" Asian Journal of Andrology, Asian Journal of Andrology, Jan. 2010, vol. 12, No. 1, pp. 36-46.
Aziz et al. "Novel association between sperm reactive oxygen species production, sperm morphological defects, and the sperm deformity index," Fertility and Sterility, Feb. 2004, vol. 2, No. 81, pp. 349-354.
Benedetti et al. "Differences in blood and semen oxidative status in fertile and infertile men, and their relationship with sperm quality," Reproductive BioMedicine Online, Sep. 2012, vol. 25, No. 3, pp. 300-306.
Beresford et al. "A Systematic Review of the Role of Imaging before Salvage Radiotherapy for Post-prostatectomy Biochemical Recurrence," Clinical Oncology, Feb. 2010, vol. 22, No. 1, pp. 46-55.
Brazil "Practical semen analysis: from A to Z," Asian Journal of Andrology, Jan. 2010, vol. 12, No. 1, pp. 14-20.
Caro et al. "Potencial de Oxidorreduccion del Espermio en Relacion con la Fertilidad," Archivos de Medicina Experimental; Trabajos del Instituto Nacional de Ciencias Medicas, Es, 1954, vol. 17, No. 3, pp. 375-405.
Haghighian et al. "Randomized, triple-blind, placebo-controlled clinical trial examining the effects of alpha-lipoic acid supplement on the spermatogram and seminal oxidative stress in infertile men," Fertility and Sterility, 2015, vol. 104, No. 2, pp. 318-324.
Ho et al. "Correlation Between Semen Parameters and the Hamster Egg Penetration Test (HEPT) Among Fertile and Subfertile Men in Singapore," Journal of Andrology, Jan./Feb. 2007, vol. 28, No. 1, pp. 158-163.
Macanovic et al. "Correlation between Sperm Parameters and Protein Expression of Antioxidative Defense Enzymes in Seminal Plasma: A Pilot Study," Disease Markers, 2015, 436236, 5 pages.
Menkveld et al. "Semen parameters, including WHO and strict criteria morphology, in a fertile and subfertile population: an effort towards standardization of in-vivo thresholds," Human Reproduction, Jun. 2001, vol. 16, No. 6, pp. 1165-1171.
Lian et al. "Antioxidant supplementation overcomes the deleterious effects of maternal restraint stress-induced oxidative stress on mouse oocytes," Reproduction, Sep. 2013, vol. 146, No. 6, pp. 559-568.
Michael et al. "Effect of antioxidant supplementation on semen quality and reactive oxygen species of frozen-thawed canine spermatozoa," Theriogenology, vol. 68, No. 2, 2007, pp. 204-212.
Mortimer et al. "Sperm Morphology Assessment—Historical Perspectives and Current Opinions," Journal of Andrology, Mar.-Apr. 2001, vol. 22, No. 2, pp. 192-205.
Ombelet et al. "Semen parameters in a fertile versus subfertile population: a need for change in the interpretation of semen testing." Human Reproduction, May 1997, vol. 12, No. 5, pp. 987-993.
Pons-Rejraji et al. "Role of reactive oxygen species (ROS) on human spermatozoa and male infertility," Gynecologie Obstetrique & Fertilite, Jun. 2009, vol. 37, No. 6, pp. 529-535 (Abstract only).

Rad et al. "Serum Levels of Melatonin and Oxidative Stress Markers and Correlation between Them in Infertile Men," Journal of Caring Sciences, 2013, vol. 2, No. 4, pp. 287-294.
Roth et al. "Assessing the antioxidative status in critically ill patients," Current Opinion in Clinical Nutrition and Metabolic Care, 2004, vol. 7, pp. 161-168.
Saleh et al. "Negative effects of increased sperm DNA damage in relation to seminal oxidative stress in men with idiopathic and male factor infertility," Fertility and Sterility, Jun. 2003, vol. 79, Suppl 3: 1597-1605.
Sharma et al. "Effect of Time on Oxidation-Reduction Potential in Semen and Seminal Plasma," Fertility and Sterility, Sep. 2015, vol. 3, No. 104, Supplement, abstract P-552, p. e295.
Svobodova et al. "Comparison of reactive oxygen species production in neat semen and washed spermatozoa," Ceska Gynekol, 2009, vol. 74, No. 6, pp. 399-403 (Abstract only).
Van Den Hoven et al. "Status of sperm morphology assessment: an evaluation of methodology and clinical value," Fertility and Sterility, Jan. 2015, vol. 103, No. 1, pp. 53-58.
Veglia et al. "Age- and gender-related oxidative status determined in healthy subjects by means of XOY-SCORE, a potential new comprehensive index," Biomarkers, Nov.-Dec. 2006, vol. 11, No. 6, pp. 562-573.
Wright et al. "Sperm DNA damage caused by oxidative stress: modifiable clinical, lifestyle and nutritional factors in male infertility," Reproductive Biomedicine Online, Jun. 2014, vol. 28, No. 6, pp. 684-703.
Zhi et al. "The reliability of clinical dynamic monitoring of redox status using a new redox potential (ORP) determination method," Redox Report, Jul. 2013, vol. 18, No. 2, pp. 63-70.
Zorn et al. "Seminal reactive oxygen species as predictors of fertilization, embryo quality and pregnancy rates after conventional in vitro fertilization and intracytoplasmic sperm injection," International Journal of Andrology, Oct. 2003, vol. 26, No. 5, pp. 279-285 (Abstract only).
International Search Report and Written Opinion for International (PCT) Patent Application No. PCT/US15/62455, dated May 17, 2016 10 pages.
International Preliminary Report on Patentability for International (PCT) Patent Application No. PCT/US2015/062455, dated Jun. 8, 2017 7 pages.
Extended Search Report for European Patent Application No. 15862884.2, dated May 23, 2018 9 pages.
Official Action for U.S. Appl. No. 15/466,140, dated Aug. 30, 2017 7 pages Restriction Requirement.
Official Action for U.S. Appl. No. 15/466,140, dated Dec. 28, 2017 18 pages.
Notice of Allowance for U.S. Appl. No. 15/466,140, dated Aug. 7, 2018 9 pages.
English Translation of Official Action for China Patent Application No. 201580062907.3, dated Aug. 1, 2018.
Official Action with English Translation for Japan Patent Application No. 2017/526119, dated Feb. 26, 2019 5 pages.
Official Action with English Translation for Israel Patent Application No. 252304, dated Dec. 13, 2018 7 pages.
Official Action for Australia Patent Application No. 2015353639, dated Jul. 1, 2019, 5 pages.
Official Action for European Patent Application No. 15862884.2, dated Aug. 8, 2019, 3 pages.
Official Action with English Translation for Japan Patent Application No. 2017-526119, dated Sep. 10, 2019, 4 pages.

DETERMINATION OF FERTILITY POTENTIAL FROM THE OXIDATION-REDUCTION POTENTIAL OF A BIOLOGICAL SAMPLE

CROSS-REFERENCE TO RELATED APPLICATIONS

This application is a continuation application of U.S. application Ser. No. 15/466,140, filed Mar. 22, 2017, which claims the benefit of priority under 35 U.S.C. § 120 and is a continuation of PCT Application No. PCT/US15/62455, filed Nov. 24, 2015, which claims the benefit of priority under 35 U.S.C. § 119(e) to U.S. Provisional Application Ser. No. 62/084,414, filed Nov. 25, 2014. The entire disclosure of each of U.S. application Ser. No. 15/466,140, PCT Application No. PCT/US15/62455 and U.S. Provisional Application Ser. No. 62/084,414 is incorporated herein by reference.

FIELD

The present invention relates to methods and apparatuses for measuring the oxidation-reduction potential (ORP) of a fluid sample and using such ORP to determine the fertility potential of a sample and/or subject.

BACKGROUND

Many biological fluids, such as whole blood, plasma, serum, semen, uterine and vaginal fluids, have oxidation-reduction potentials (ORP). Clinically, the ORP of such fluids provides the oxidative status of an animal. More particularly, the ORP of such fluids is related to health, disease and the status of biological processes.

An oxidation-reduction system, or redox system, involves the transfer of electrons from a reductant to an oxidant according to the following equation:

$$\text{oxidant} + ne^- \leftrightarrow \text{reductant} \quad (1)$$

where $ne^-$ equals the number of electrons transferred. At equilibrium, the redox potential (E), or oxidation-reduction potential (ORP), is calculated according to the Nernst-Peters equation:

$$E(ORP) = E_o - RT/nF \ln [\text{reductant}]/[\text{oxidant}] \quad (2)$$

where R (gas constant), T (temperature in degrees Kelvin) and F (Faraday constant) are constants. $E_o$ is the standard potential of a redox system measured with respect to a hydrogen electrode, which is arbitrarily assigned an $E_o$ of 0 volts, and n is the number of electrons transferred. Therefore, ORP is dependent on the total concentrations of reductants and oxidants, and ORP is an integrated measure of the balance between total oxidants and reductants in a particular system. As such, ORP provides a measure of the overall oxidative status of a body fluid or tissue of a patient.

Oxidative stress is caused by a higher production of reactive oxygen and reactive nitrogen species or a decrease in endogenous protective antioxidative capacity. Oxidative stress has been related to various diseases and aging, it has been found to occur in all types of illnesses, and it has been shown to affect numerous biological processes including conception and pregnancy. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613; Agarwal et al., *Reproductive Biology and Endocrinology*, 3:28: 1-21 (2005); Rad et al., *J. Caring Sciences*, 2(4): 287-294 (2013). Several investigations have shown a close association between the oxidative status of a patient and the patient's outcome. See Roth et al., *Current Opinion in Clinical Nutrition and Metabolic Care*, 7:161-168 (2004).

Oxidative stress in patients has been evaluated by measuring various individual markers. See, e.g., Veglia et al., *Biomarkers*, 11(6): 562-573 (2006); Roth et al., *Current Opinion in Clinical Nutrition and Metabolic Care*, 7:161-168 (2004); U.S. Pat. No. 5,290,519 and U.S. Patent Publication No. 2005/0142613. However, such measurements are often unreliable and provide conflicting and variable measurements of the oxidative status of a patient. See Veglia et al., *Biomarkers*, 11(6): 562-573 (2006); Roth et al., *Current Opinion in Clinical Nutrition and Metabolic Care*, 7:161-168 (2004). The measurement of multiple markers which are then used to provide a score or other assessment of the overall oxidative status of a patient has been developed to overcome the problems of using measurements of single markers. See Veglia et al., *Biomarkers*, 11(6): 562-573 (2006); Roth et al., *Current Opinion in Clinical Nutrition and Metabolic Care*, 7:161-168 (2004). Although such composite approaches are more reliable and sensitive than measurements of a single marker, they are complex and time consuming. Thus, there is a need for a simpler and faster method for reliably measuring the overall oxidative status of a patient.

The oxidation/reduction potential can be measured electrochemically. Electrochemical devices for measuring ORP of blood, blood products, and other biological fluids, typically require large sample volumes (that is, ten to hundreds of milliliters) and long equilibrium periods. Furthermore, the electrochemical devices have large, bulky electrodes that require cleaning between sample measurements. Such electrochemical devices are poorly suited for routine clinical diagnostic testing. It has been suggested to use electrodes that have undergone treatment to prevent biofouling. However, such devices necessarily involve complex manufacturing techniques. Moreover, conventional electrochemical devices have not provided a format that is convenient for use in a clinical setting.

The oxidative and radical characteristics of biological fluids, such as blood plasma and its blood components (such as low density lipoproteins, serum albumin, and amino acids), semen (and its components), uterine and vaginal secretions, can also be determined from photo chemiluminescence, with and without thermo-initiated free radical generation. A photo chemiluminescent system generally includes a free radical generator and a detector that measures chemiluminometric changes in the presence of an antioxidant. More specifically, to measure antioxidant presence, the biological sample (or one of its components) containing an amount of antioxidant is contacted and reacted with a known amount of free radicals. The free radicals remaining after contacting the biological sample are determined chemiluminometrically. Free radicals are measured in a similar chemiluminescent, using a known amount of antioxidants against the endogenous free radicals in the sample. These types of measurements and the detection system are not suitable for rapid, large scale measurements of biological fluid samples in a clinical setting for assessing or monitoring human or animal health.

In recent years, the proportion of men meeting the criteria for normal sperm morphology has dropped substantially. The predictive value of sperm morphology to identify infertile donors from proven donors, ranges from 98.6% to 57.9%

(Agarwal, A. et al. (2014). *Reprod Biol Endocrinol*, 12, 33; Menkveld, R., et al. (2001) *Hum Reprod*, 16, 1165-1171; Ho, L. M., et al. (2007), *J. Androl*, 28, 158-163.). Morphology was found to be better at identifying infertile donors than measures of sperm motility, concentration, total sperm count, the hamster egg penetration test (HEPT), or the sperm penetration index (Ombelet, W., et al. (1997). *Hum Reprod*, 12, 987-993.). More importantly, morphology is strongly related to pregnancy and successful in vitro fertilization (IVF) results with increased odds of implantation and pregnancy, and decreased miscarriages (van den Hoven, L., et al. (2015). *Fertil Steril*, 103, 53-58; Mortimer, D. and Menkveld, R. (2001). *J. Androl*, 22, 192-205; Abu Hassan Abu, et al. (2012). *Andrologia*, 44 Suppl 1, 571-577.). Despite the importance of this parameter, qualitative morphological measures are subject to technical, procedural, and subjective errors more so than other sperm parameter. A common semen sample can produce morphology results that vary as much as 30% (Brazil, C. (2010). *Asian Journal of Andrology*, 12, 14-20; Auger, J. (2010). *Asian Journal of Andrology*, 12, 36-46.) Thus, an unbiased, quantitative measure, representative of sperm morphology, would greatly benefit the fertility community.

In some studies, oxidative stress has been associated with infertility in men, and specifically with morphology. (Agarwal, A., et al. (2014). *Syst Biol Reprod Med*, 60, 206-216; Pons-Rejraji, H., et al. (2009). *Gynecol Obstet Fertil*, 37, 529-535; Benedetti, S. et al. (2012). *Reprod Biomed Online*, 25, 300-306; Zorn, B., et al. (2003). *Int J Androl*, 26, 279-285; Macanovic, B., et al. (2015). *Dis Markers*, 2015, 436236; Svobodova, M., et al. (2009). Ceska Gynekol, 74, 399-403.) Others studies report a more ambiguous relationship. (Svobodova, M., et al. (2009). Ceska Gynekol, 74, 399-403; Haghighian, H. K., et al. (2015). *Fertil Steril*; Beresford, M. J., et al. (2010). *Clinical Oncology*, 22, 46-55.) The difference between these studies are revealed in their methods. Most studies measure a single family of oxidants, i.e. reactive oxygen species (ROS). Others measure the post-hoc damage that accumulates under oxidative stress, i.e. lipid peroxidation. Lastly, the changes in antioxidant levels or activity have been used, i.e. total antioxidant capacity (TAC) or superoxide dismutase (SOD). With the numerous ways in which "oxidative stress" is defined by single measures, it is not unreasonable to question the role of oxidative stress in male fertility. Oxidative stress is a state in which the activity of the oxidants exceeds the capabilities of the antioxidants to quench them. Thus, there is a need for a simple measure that compares all oxidant activity to all antioxidant activity as a predictor of sperm morphology and infertility. The present invention addresses this need and provides other, related benefits as well.

SUMMARY

One embodiment is a method of evaluating the fertility potential of sperm from a subject, the method comprising measuring the oxidation-reduction potential (ORP) of a sample from the subject; comparing the measured ORP to a reference value; and determining the fertility potential of the sperm sample based on the comparison. In one embodiment, the step of measuring comprises measuring the static ORP (sORP). In one embodiment, the step of measuring comprises measuring the capacity ORP (cORP). In one embodiment, the step of measuring comprises measuring the sORP and the cORP. In one embodiment, the reference value is a value associated with fertile sperm quality parameters. In one embodiment, the reference value is a discharge reference value. In one embodiment, the reference value is a self reference value. In one embodiment, if the ORP value of the sample being tested is significantly increased compared to a reference value from a sample having a high fertility potential, characterizing the sperm sample being tested as having a low fertility potential. In one embodiment, if the ORP value of the sample being tested is essentially the same as a reference value from a sample having a high fertility potential, characterizing the sperm sample being tested as having a high fertility potential.

One embodiment of the invention is a method of determining at least one characteristic of a sperm sample from a subject, comprising: measuring the static oxidation-reduction potential (sORP) and/or the capacity oxidation-reduction potential (cORP) of a sample from the subject; comparing the measured sORP and/or cORP to a reference value; and determining the characteristic of the sperm based on the comparison. In one embodiment, the step of measuring comprises measuring the sORP. In one embodiment, the step of measuring comprises measuring the cORP. In one embodiment, the step of measuring comprises measuring the sORP and the cORP. In one embodiment, the at least one characteristic is selected from the group consisting of: the percentage of sperm cells in the sample having a healthy morphology, the percentage of motile sperm cells in the sample, the number of sperm cells in the sample and the concentration of sperm cells in the sample. In one embodiment, the reference value if a cut-off value. In one embodiment, if the measured ORP is significantly higher than the cut-off value, sperm sample is designated as having one or more characteristics selected from the group consisting of a high percentage of sperm cells in the sample having an abnormal morphology, a high percentage of sperm cells in the sample having abnormal motility (e.g., reduced motility), a lower than normal number of sperm cells and an abnormally low concentration of sperm cells in the sample. In one embodiment, if the measured ORP is less than, or equal to, the cut-off value, the sample is designated as having one or more characteristics selected from the group consisting of a high percentage of sperm cells in the sample having an normal morphology, a high percentage of sperm cells in the sample having normal motility, at last a normal number of sperm cells and at least a normal concentration of sperm cells. In one embodiment, if the measured ORP is less than, or equal to, the cut-off value, the sample is designated as being of goof quality or as having high fertility potential.

One embodiment of the invention is a method of evaluating the competence of an egg from a subject, comprising: measuring the static oxidation-reduction potential (sORP) and/or the capacity oxidation-reduction potential (cORP) of a sample from the subject; comparing the measured sORP and/or cORP to a reference value; and classifying the egg as competent or incompetent based on the comparison. In one embodiment, the step of measuring comprises measuring the sORP. In one embodiment, the step of measuring comprises measuring the cORP. In one embodiment, the step of measuring comprises measuring the sORP and the cORP. In one embodiment, the reference value is a normal reference value. In one embodiment, the reference value is a discharge reference value. In one embodiment, the reference value is a self reference value. In one embodiment, if the sORP value of the sample being tested is significantly increased compared to a reference value indicating a competent egg, characterizing the egg being tested as being incompetent. In one embodiment, if the ORP value of the sample being tested is essentially similar to a reference value indicating a competent egg, characterizing the egg being tested as being competent. In one embodiment, the sample is selected from the group consisting of a vaginal sample, a follicular sample and a uterine sample.

One embodiment of the present invention is a method of evaluating the fertility status of a subject, comprising: measuring the static oxidation-reduction potential (sORP) and/or the capacity oxidation-reduction potential (cORP) of a sample from the subject; comparing the measured sORP and/or cORP to a reference value; and determining the fertility status of the subject based on the comparison. In one embodiment, the step of measuring comprises measuring the sORP. In one embodiment, the step of measuring comprises measuring the cORP. In one embodiment, the step of measuring comprises measuring the sORP and the cORP. In one embodiment, the reference value is a normal reference value. In one embodiment, the reference value is a discharge reference value. In one embodiment, the reference value is a self reference value. In one embodiment, if the ORP value of the sample being tested is significantly increased compared to a reference value indicating reduced fertility, identifying the subject has having reduced fertility. In one embodiment, if the ORP value of the sample being tested is essentially similar to a reference value indicating fertility, identifying the subject has being fertile, or achieving normal fertility. In one embodiment, the sample is selected form the group consisting of a semen sample, a seminal fluid sample, a uterine sample, a vaginal sample or a follicular sample.

One embodiment of the present invention is a method of evaluating the likelihood that a fertilized egg will establish and maintain a successful pregnancy, comprising: measuring the static oxidation-reduction potential (sORP) and/or the capacity oxidation-reduction potential (cORP) of medium in which the fertilized egg is being cultured; comparing the measured sORP and/or cORP to a reference value; and determining the likelihood of the egg to establish and maintain a successful pregnancy based on the comparison. In one embodiment, the step of measuring comprises measuring the sORP. In one embodiment, the step of measuring comprises measuring the cORP. In one embodiment, the step of measuring comprises measuring the sORP and the cORP. In one embodiment, the reference value is a normal reference value. In one embodiment, the reference value is a discharge reference value. In one embodiment, the reference value is a self reference value. In one embodiment, if the ORP value of the sample being tested is significantly increased compared to a reference value that indicates an egg is likely to establish and maintain a successful pregnancy, the fertilized egg being tested is identified as being unlikely to establish and maintain a successful pregnancy. In one embodiment, if the ORP value of the sample being tested is essentially similar to a reference value that indicates an egg is likely to establish and maintain a successful pregnancy, the fertilized egg being tested is identified as being likely to establish and maintain a successful pregnancy.

One embodiment of the present invention is a method of improving the chances that a fertilized egg will establish and maintain a successful pregnancy, comprising: measuring the static oxidation-reduction potential (sORP) and/or the capacity oxidation-reduction potential (cORP) of medium in which the fertilized egg is being cultured; comparing the measured sORP and/or cORP to a reference value; and determining the time for transfer of the fertilized egg into the uterus based on the comparison. In one embodiment, parity of the sORP and/or cORP with a threshold value indicates the egg should be transferred to the uterus. In one embodiment, the threshold value represents the sORP and/or cORP value(s) above which the chance of establishing and maintaining a successful pregnancy is significantly reduced compared to transfers performed with fertilized eggs having the threshold value or a lower value.

In all of the foregoing embodiments, the step of measuring can be measuring the sORP, measuring the cORP or measuring the sORP and the cORP. In addition, the reference values in all of the foregoing embodiments can be one or more of a normal reference value, a condition specific reference value and a self reference value.

DETAILED DESCRIPTION

Figure 1:
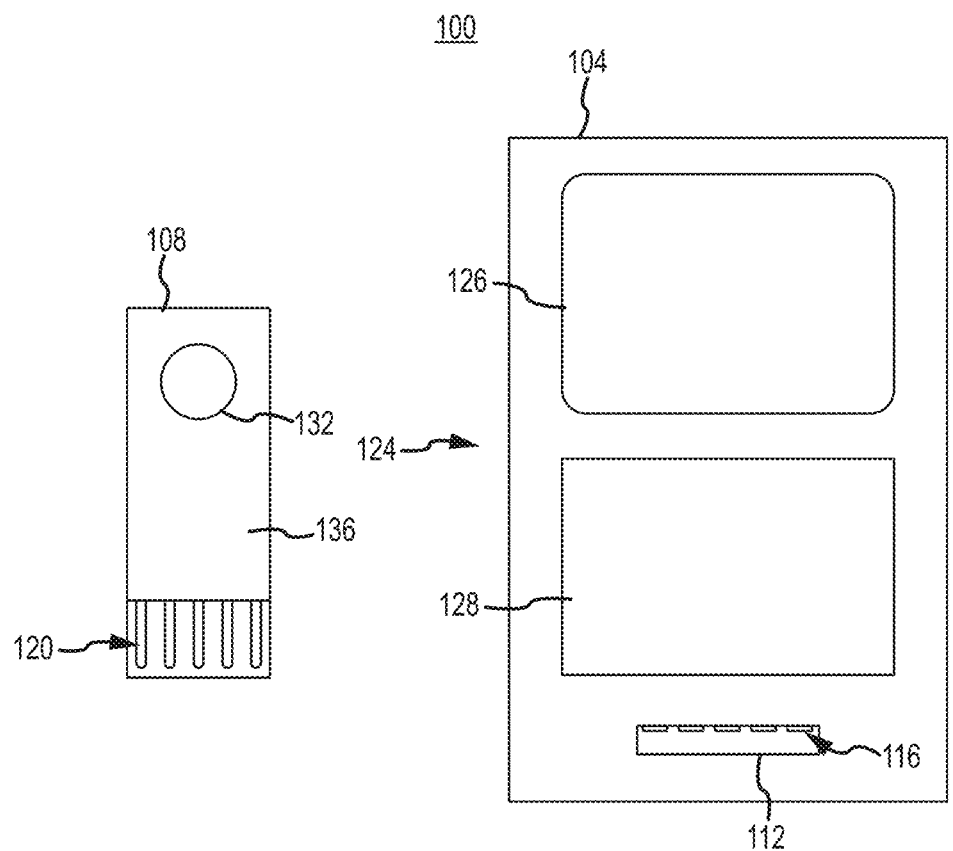
FIG. 1 depicts components of a system for measuring the oxidation-reduction potential capacity of a fluid in accordance with embodiments of the present invention.

Embodiments of the present invention provide systems and methods for measuring oxidation-reduction potential (ORP) characteristics (i.e., static oxidation-reduction potential (sORP) and/or oxidation-reduction capacity (cORP)) of a fluid that are suitable for rapid, routine clinical diagnostic testing and methods of using the system to evaluate or monitor the status of a subject. The system generally includes a test strip and a readout device. More particularly, embodiments of the present invention can determine the ORP characteristics of a body fluid of a patient in a convenient and timely manner. A biological sample of a patient that can be used in the method of invention can be any body fluid. Suitable body fluids include a blood sample (e.g., whole blood, serum or plasma), urine, saliva, cerebrospinal fluid (CSF), tears, semen, seminal fluid, vaginal or uterine secretions, follicular fluid, amniotic fluid and cord blood. Also, lavages, tissue homogenates, components of body fluids (e.g., blood cells, spermatozoa, etc.) and cell lysates can be utilized and, as used herein, "body fluid" includes such preparations. Preferably, the body fluid is blood, plasma, semen or seminal fluid, vaginal fluid, uterine fluid or follicular fluid. In some embodiments, the fluid can be a cell culture fluid such as, for example, cell culture medium used in the culture of spermatozoa and/or ovum.

The test strip generally includes a substrate, a reference cell, a counter electrode, a working electrode, a reference electrode, and a sample chamber. In general, by placing a fluid sample in the sample chamber, an electrical connection is established between the reference cell, the counter electrode, the working electrode, and the reference electrode. The test strip can then be connected to a readout device, for the determination of a static ORP value and an ORP capacity value.

The readout device generally includes contacts to electrically interconnect the readout device to the various electrodes included in the test strip. In accordance with embodiments of the present disclosure, the readout device includes an analog front end. The analog front end generally functions to provide a controlled current that can be sent across the fluid in the sample chamber through an electrical connection to the counter electrode and the working electrode. In addition, the analog front end is operable to generate a voltage signal that represents the potential difference between the reference electrode and the working electrode. An analog to digital (ADC) converter is provided to convert the voltage signal representing the reference electrode to working electrode potential difference to a digital signal. A digital to analog converter (DAC) is provided to convert a digital control signal to analog signals in connection with the provision of the controlled current to the test strip. A controller interfaces with the ADC and the DAC. Moreover, the controller can include or comprise a processor that implements programming code controlling various functions of the readout device, including but not limited to controlling the current supply to the test strip, and processing the potential difference measurement signal. The controller can operate in association with memory. In addition, the readout device includes a user interface, and a power supply.

FIG. 1 depicts components of a system 100 for measuring the oxidation-reduction potential (ORP) value, including but not limited to the static oxidation-reduction value (sORP) and/or the oxidation-reduction capacity value (cORP), of a fluid sample in accordance with embodiments of the present disclosure. As used herein, the sORP is a measured potential difference or voltage across a fluid sample such as a measured potential difference or voltage across a fluid sample placed in a test strip that includes a reference cell as described herein. The cORP as used herein is a measure of the quantity of charge provided to a fluid sample over a defined period such as can be measured in a test strip as described herein. Accordingly, the cORP can be viewed as the capacity of a fluid sample to absorb an electrical charge supplied as a current over some defined period. For example, the period can be defined by a start point corresponding to the initiation of current supply to a sample and an endpoint such as an inflection point or a midpoint between a first and a second inflection point. In general, the system 100 includes a readout device 104, which can implement a galvanometer, and a test strip 108. The readout device 104 includes a connector or readout aperture 112 for electrically interconnecting readout contacts 116 of the readout device 104 to electrode contacts 120 provided as part of the test strip 108. The readout device 104 can also incorporate a user interface 124, which can include a user output 126, such as a display, and a user input 128, such as a keypad. In accordance with still other embodiments, the user interface 124 can comprise an integrated component, such as a touch screen interface. In addition to providing contacts 120 for interconnecting the test strip 108 to the readout device 104, the test strip 108 includes a sample chamber aperture 132 formed in a test strip overlay 136, to receive a fluid sample in connection with the determination of an ORP value of that fluid sample.

Figure 2:
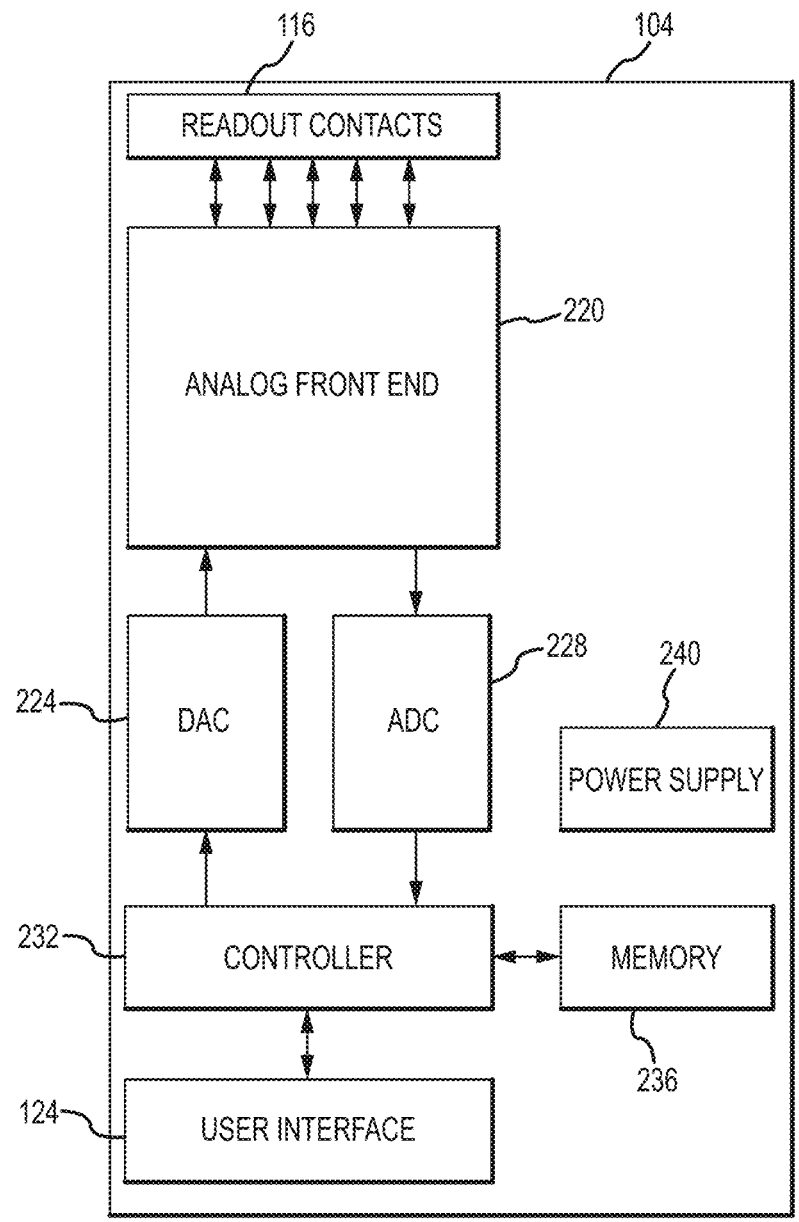
FIG. 2 illustrates components of a readout device in accordance with embodiments of the present disclosure.

FIG. 2 illustrates additional components and features of a readout device 104 in accordance with embodiments of the present disclosure. As shown, the readout contacts 116 are interconnected to an analog front end 220. As described in greater detail elsewhere herein, the analog front end 220 generally functions to provide a controlled current that is passed between a counter electrode and a working electrode of the test strip 108. In addition, the analog front end 220 functions to provide a voltage signal representing a potential difference between a reference electrode and the working electrode of the test strip 108. In accordance with still further embodiments, the analog front end 220 can include a strip detect circuit, to provide a signal indicating the interconnection of a test strip 108 to the readout device 104.

The analog front end 220 generally receives control signals from a digital to analog (DAC) converter 224. Signals output by the analog front end 220 are generally provided to an analog to digital converter (ADC) 228. The DAC 224 and ADC 228 are in turn connected to a controller 232. The controller 232 may comprise a processor that is operable to execute instructions stored in memory as part of the controller 232, or as a separate memory device 236. For example, the processor, executing instructions stored in memory 236, can implement a process according to which the current supplied to the test strip 108 is controlled. In addition, the controller 232 can execute instructions stored in memory 236 to record the quantity of current supplied to the test strip 108, to detect an inflection point in the voltage potential between electrodes of the test strip 108, and to calculate an ORP capacity. The memory 236 can also function as storage for data, including but not limited to intermediate and/or final ORP values. The controller 232, for example, can comprise a general purpose programmable processor or controller or a specially configured application integrated circuit (ASIC).

The user interface 124 generally operates to provide user input to the controller 232. In addition, the user interface 124 can operate to display information to a user, including but not limited to the status of the readout device 104 or of the system 100 generally, a sORP value, and a cORP value.

The readout device 104 also generally includes a power supply 240. Although not shown in the figure, the power supply 240 is generally interconnected to power consuming devices via a power supply bus. The power supply 240 may be associated with a battery or other energy storage device, and/or line power.

Figure 3:
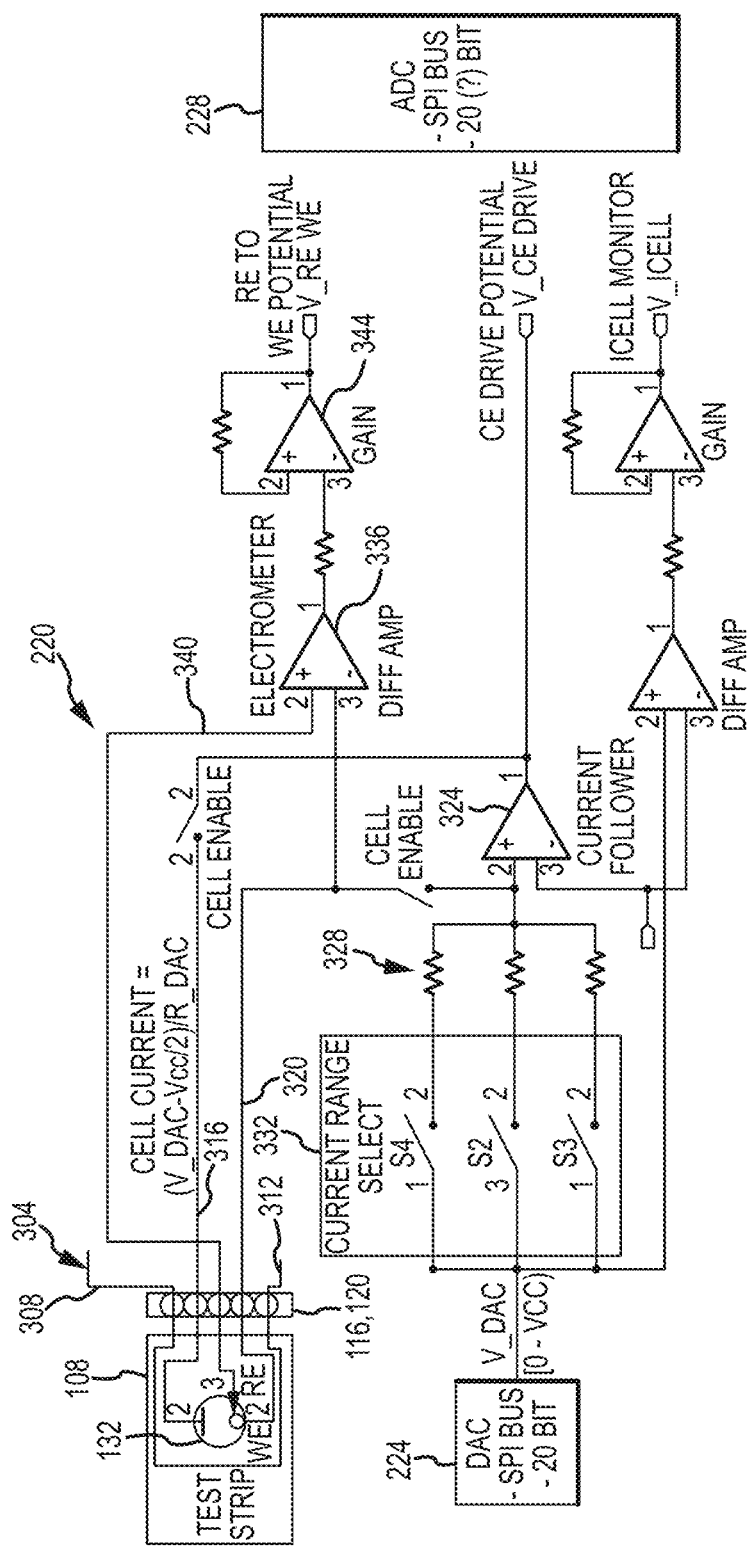
FIG. 3 illustrates further aspects of a readout device in accordance with embodiments of the present disclosure.

With reference now to FIG. 3, additional features of a system 100 in accordance with embodiments of the present disclosure are depicted. More particularly, details of the analog front end 220 and of the electrical circuit associated with the test strip 108 are depicted. As shown, the readout contacts 116 interconnect to the electrode leads or contacts 120, to electrically connect the analog front end 220 to the test strip 108. In the illustrated embodiment, the analog front end 220 includes a test strip sense circuit 304. The test strip sense circuit 304 includes a test strip detection supply lead 308 and a test strip detection input lead 312. In general, when a suitable test strip 108 is operatively connected to the readout device 104, continuity between the test strip detect supply lead 308 and the test strip detection input lead 312 is established, allowing a test strip detect signal indicating that a test strip 108 is present to be passed between the supply 308 and the input 312 leads. Moreover, a test strip 108 can incorporate a resistor or other component to modify the test strip detect signal, to indicate to the readout device 104 characteristics of the particular test strip 108 that has been interconnected to the readout device 104, such as the voltage value of a reference cell incorporated into the test strip 108. In response to sensing the presence of a test strip 108, the readout device 104 can operate to provide an interrogation signal in the form of a controlled current to the test strip 108.

The current is provided by the readout device 104 to the sample chamber 132 of the test strip 108 via a counter electrode lead 316 and a working electrode lead 320. More particularly, the current may be supplied to the counter electrode lead 316 from the output of a current follower 324, while the working electrode 320 can be provided as an input to that current follower 324. In addition, a set of current range select resistors 328 and associated switches 332 can be controlled by the DAC 224, as directed by the controller 232, for example depending on the characteristics of the interconnected test strip 108. In addition, the DAC 224, as directed by the controller 232, can control the input to the current follower 324 to in turn control the amount of current supplied to the test strip 108 by the current electrode lead 316. The DAC 224, as directed by the controller 232, can also operate various switches and/or amplifiers to control the operating mode of the analog front end 220.

The analog front end 220 additionally includes an electrometer 336 that receives a first input signal from a reference electrode lead 340 and a second input signal from the working electrode lead 320. The output from the electrometer 336 generally represents the potential difference between the reference electrode lead 340 and the working electrode lead 320. The signal output by the electrometer 336 can be amplified in a gain circuit 344, and output to the ADC 228.

Figure 4:
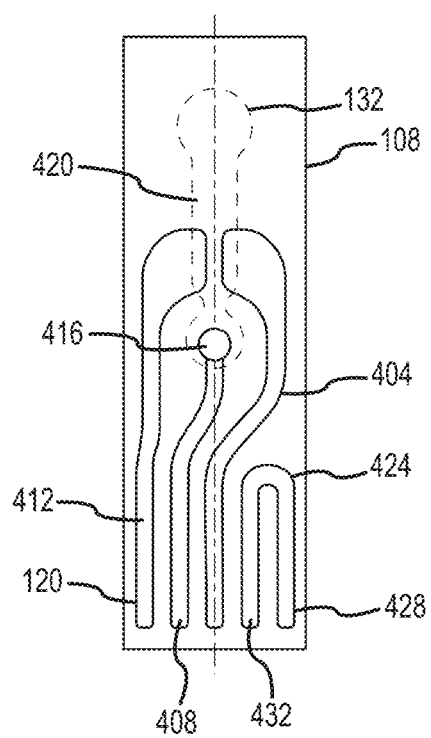
FIG. 4 depicts a test strip in accordance with embodiments of the present invention.

FIG. 4 depicts aspects of a test strip 108 in accordance with embodiments of the present invention. More particularly, the view presented by FIG. 4 shows the test strip 108 with the test strip overlay 136 removed. In general, the test strip 108 includes a working electrode 404, a reference electrode 408, and a counter electrode 412. In addition, the test strip 108 includes a reference cell 416. By placing a fluid sample within a sample chamber region 420, the working electrode 404, the reference electrode 408, the counter electrode 412, and the reference cell 416 are placed in electrical contact with one another. Moreover, by placing the electrode contacts 120 corresponding to the counter electrode 412, the working electrode 404 and the reference electrode 408 in contact with the readout contacts 116 corresponding to the counter electrode lead 316, the working electrode lead 320, and the reference electrode lead 340 respectively, the test strip 108 is operatively connected to the readout device 104. Accordingly, a supply current provided to the test strip 104 can be sent across the fluid sample, between the counter electrode 412 and the working electrode 404 by the readout device 104. Moreover, the potential difference between the reference electrode 408 and the working electrode 404 can be sensed by the readout device 104. In accordance with further embodiments of the present disclosure, the test strip 108 can include a test strip detect circuit 424, that includes an input 428 and an output 432. The test strip detect circuit 424 can, in addition to the input 428 and the output 432, include a resistor or other component for modifying a test strip sense signal provided by the readout device 104, to indicate to the readout device 104 an identification of the test strip 108.

To measure the cORP or antioxidant reserve, the sample is titrated with a linearly increasing oxidizing current between a counter and working electrode to exhaust the relevant antioxidants at the working electrode while monitoring the voltage between the working and reference electrodes. The result is a time vs. voltage curve and a time vs. current curve. The time versus voltage curve is used to find an inflection point where the voltage is changing the fastest (antioxidants are exhausted so system tries to find a new equilibrium). The time at maximum velocity (i.e., at the inflection point) is referred to as the transition time. The capacity or cORP is then the integral of the current profile from the beginning to the transition time with units of uC.

Calculation of the transition time may be accomplished several ways including noise filtration, curve fitting and standard numerical differentiation techniques. Usually the unfiltered numerical derivative is noisy, making finding maxima difficult or unreliable. To that end one technique is to curve fit the time versus voltage profile with a polynomial (5th-7th order is usually sufficient) and directly differentiating the resulting polynomial analytically. This approach has the advantage of very smooth derivatives making the determination of the transition time robust as long as the fit is good.

Figure 5:
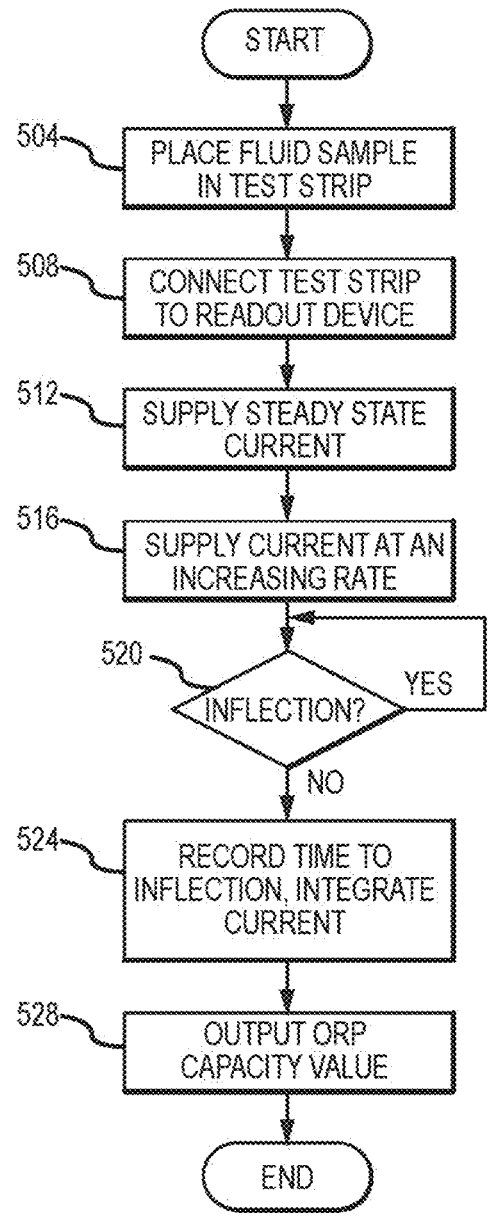
FIG. 5 is a flowchart depicting aspects of a method for measuring oxidation-reduction potential capacity in accordance with embodiments of the present disclosure.

FIG. 5 is a flowchart illustrating aspects of the operation of a system 100 for determining the ORP, including but not limited to the cORP, of a fluid sample in accordance with embodiments of the present invention. In general, the method includes obtaining a fluid sample and placing the fluid sample in the sample chamber 420 of a test strip 108 (step 504). At step 508, the test strip 108 is connected to the readout device 104 (step 508). In general, while the readout device 104 is in an on or standby mode, an electrical signal may be output by the test strip detection output lead 308. By connecting a suitable test strip 108 to a readout device 104, continuity between the test strip detect output lead 308 and the test strip detect input lead 312 is established. In addition, the signal received at the test strip detect input lead 312 can provide an indication of characteristics of the test strip 108, which can in turn be used to control aspects (e.g., a current range) of a current supplied to the test strip 108. Such characteristics can include but are not limited to the type and composition of the test strip electrodes 404, 408 and 412, and the potential of the reference cell 416.

At step 512, a current can be supplied by the readout device 104 to the counter electrode 412 of the test strip 108. More particularly, a current can be passed between the counter electrode 412 and the working electrode 404 by the counter electrode lead 316 and the working electrode lead 320. In accordance with embodiments of the present disclosure, the current that is supplied to the test strip 108 is controlled by the controller 232 of the readout device 104. More particularly, the current can be provided for at least a first segment of time at a selected, steady state level. The first segment of time can be a fixed time period. Alternatively, the first segment of time can expire once a determination has been made that the potential difference sensed by the readout device 104 between the reference electrode 408 and the working electrode 404 has a rate of change that is less than some selected amount. In accordance with still other embodiments, a combination of parameters may be applied to determine the time period over which the current is supplied at a steady state. Moreover, in accordance with other embodiments, no current is supplied during the first period of time (i.e. the supplied current during the first segment of time is zero). As can be appreciated by one of skill in the art after consideration of the present disclosure, while no current is supplied and while the rate of change of that potential difference is zero or less than some selected amount, the potential difference measured by the readout device 104 between the reference electrode 408 and the working electrode 404 is equal to the sORP of the fluid sample.

After the first segment of time has expired, the current can be supplied at an increasing rate (step 516). For example, the amount can be increased linearly, as a step function, exponentially, according to a combination of different profiles, or in any other fashion. For instance, the current can be increased linearly from 0 amps at a specified rate until an endpoint is reached. As another example, the amount can be stepped from 0 amps to some non-zero value, and that non-zero value can be provided at a steady rate for some period of time, or can be provided at an increasing rate according to some function. At step 520, a determination can be made as to whether an inflection point in the potential difference monitored between the reference electrode 408 and the working electrode 404 has been detected. More particularly, the reference electrode lead 340 and the working electrode lead 320 connect the reference electrode 408 and the working electrode 404 respectively to the electrometer 336, which outputs a signal representing the potential difference between the reference 408 and the working 404 electrodes. The analog to digital converter 228 then converts the signal representing the potential difference between the reference 408 and working 404 electrodes to a digital signal that is provided to the controller 232. If an inflection point has been detected, the readout device 104, and in particular the controller 232, can record the time from which current was first supplied to the time at which the inflection point is reached. In addition, the controller 232 can integrate the current signal to determine an amount of charge that has been supplied to the fluid sample up to the time at which the inflection point is reached (step 524). In accordance with embodiments of the present disclosure, a first inflection point (e.g., a point at which the voltage measured across a fluid sample while a current is being supplied is at a local maximum rate of change) is used as the point at which integration of the current is stopped. However, multiple inflection points can be observed in the measured voltage. Accordingly, rather than using the first observed inflection point as the end point for integration, a subsequent inflection point can be used. As yet another example, a time determined with reference to multiple inflection points, such as a midpoint between two observed inflection points or an average time of multiple observed inflection points can be used as the end point of the integration for purposes of determining the cORP of a fluid sample. At step 528, the determined quantity of charge or a value derived from the determined quantity of charge can be output to a user as an ORP capacity (cORP) value for the fluid sample, for example through the output device 128 facility of a user interface 124 provided as part of or interconnected to a readout device 104. For example, the cORP value can be defined as one over the quantity of charge. The process can then end.

Figure 6:
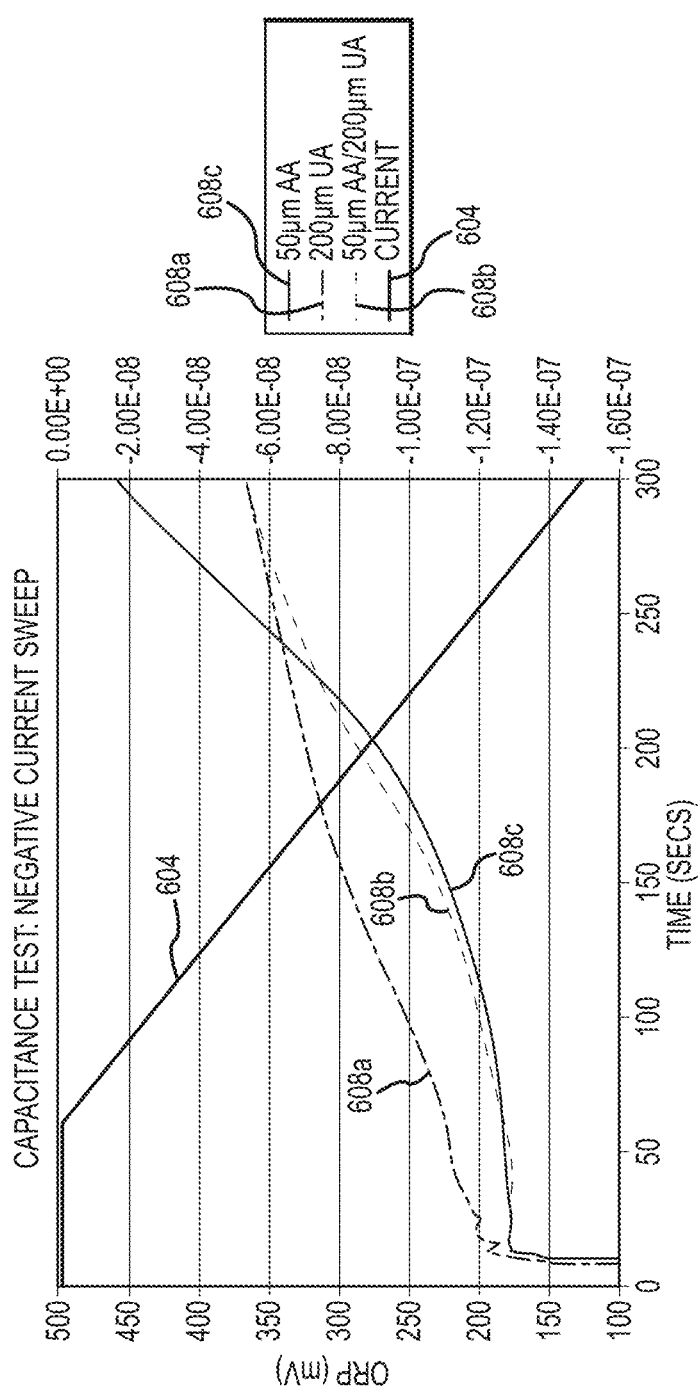
FIG. 6 is a graph depicting a supplied current and a measured potential difference over time.

FIG. 6 depicts the current, shown as line 604, supplied by a readout device 104 to an interconnected test strip 108 over time. In addition, sample measured potential difference values 608a-c for different exemplary samples are depicted. As can be understood by one of skill in the art after consideration of the present disclosure, although three potential difference values 608 are shown, a current 604 is provided to only one fluid sample during determination of an ORP value. As can also be appreciated by one of skill in the art after consideration of the present disclosure, the ramped portion of the current 604 is shown sloping in a downward direction, because it depicts an oxidizing current. In addition, it can be appreciated that the area between the current curve 604 and a current value of zero for a selected period of time represents a quantity of charge provided to a fluid sample held in a test strip 108. Accordingly, this quantity of charge can be used to provide a measurement of the ORP capacity (cORP) of the fluid sample. Moreover, the voltage curves 608 represent a static ORP (sORP) value of a respective fluid sample at different points in time. The area under the current curve 604 (which is above the curve 604, between that curve and a current of zero in FIG. 6) that is used to determine the cORP can have a start point at a first point in time and an end point at a second point in time. As an example, the start point for integration of the current 604 can be selected as a point at which the observed sORP signal or reading has stabilized. For instance, in the example of FIG. 6, the potential difference values have stabilized after about 50 seconds have elapsed. Moreover, in this example no current is being supplied to the sample by the readout device 104 during the first segment of time leading up to the start point at which current is supplied. That start point can also correspond to the time at which the current 604 begins to be applied at an increasing rate. In accordance with embodiments of the present disclosure, where a curve 608 reaches an inflection point, for example the point at which the rate of change in the measured potential difference is at a maximum (i.e., a point of maximum slope), the integration of the current signal 604 is stopped. For example, looking at curve 608b, an inflection point can be seen at about 200 seconds, and integration of the current 604 can thus be performed during the period beginning at 50 seconds and ending at 200 seconds. Alternatively, the integration of the current signal 604 can be stopped after some predetermined period of time. As yet another alternative, the integration of the current signal 604 can be stopped at the earlier of the observation of an inflection point or the expiration of a predetermined period of time.

As can be appreciated by one of skill in the art after consideration of the present disclosure, the measurement of the sORP value can be in units of Volts, and the integration of the current signal or value 604 therefore gives a value representing a quantity of charge in Coulombs. cORP values, as a measure of a quantity of charge, is expressed herein as one over the quantity of charge in Coulombs. In particular, by taking the inverse of the observed quantity of charge, a more normal distribution is obtained, facilitating the application of parametric statistics to observed ORP values. As used herein, the terms ORP capacity, inverse capacity levels, inverse capacity ORP or ICL are all equivalent to cORP as defined above. It will be appreciated that expression of cORP as one over a quantity of charge encompasses alternative equivalent expressions.

As noted above, higher than normal values of sORP are indicative of oxidative stress and are generally considered to be a negative indication for the subject being evaluated. cORP is a measure of a subject's capacity to withstand oxidative insult. Thus, it is generally a positive indication for a subject to have a normal or higher capacity to withstand oxidative insult. Since cORP is defined as the inverse of the quantity of charge to reach a voltage inflection point, a higher cORP value is indicative of a lesser capacity to withstand oxidative insult, and likewise, a lower cORP value is indicative of a greater capacity to withstand oxidative insult.

The present invention includes embodiments for monitoring or evaluating the health of patients with regard to their reproductive ability (e.g., fertility, ability to conceive, etc.), by determining the ORP characteristics of a biological sample of the patient. Typically, the ORP characteristics of the patient are compared to an ORP characteristic reference value or values that are relevant to that patient. As used herein, a reference value can be an ORP characteristic of the patient from a time when the patient did not have the condition in question (e.g., when he/she was fertile) or from an earlier time period when the patient had the condition in question (for purposes of monitoring or evaluating the condition or treatment thereof). Such reference values are referred to as self reference values. For example, reference values can also include initial, maximum and ending reference values, such as when ORP characteristics are evaluated over a time frame such as when a patient was known to be fertile (initial), and at a time when a patient is known to be sub-fertile or infertile (ending). Alternatively, a reference value can be an ORP characteristic of a relevant healthy population (e.g., a fertile population that is matched in one or more characteristics of species, age, sex, ethnicity, etc.). Such reference values are referred to as normal reference values. Further, a reference value can be an ORP characteristic of a relevant population similarly situated as the patient (e.g., a population having the same or similar condition (e.g., sub- or infertility) as the patient for which the patient is being treated and preferably, one that is also matched in one or more characteristics of species, age, sex, ethnicity, etc.). Such a reference value is referred to as a condition specific reference value. For example, a condition specific reference value can be an ORP value obtained from a sub-fertile or infertile individual, an incompetent egg or a sperm sample having low fertility potential.

As used herein, a subject is any individual for whom a biological sample is being tested for an ORP characteristic. The term subject can include patient if the subject is an individual being treated by a medical professional. The terms subject and patient can refer to any animal, including humans and non-human animals, such as companion animals (e.g., cats, dogs, horses, etc.) and livestock animals (i.e., animals kept for food purposes such as cows, goats, chickens, etc.). Preferred subjects include mammals and most preferably include humans.

As used herein, the terms, egg, oocyte, ovum, and the like, can be used interchangeably to refer to a female reproductive cell that has not yet been fertilized. Likewise, the terms sperm and spermatozoa can be used interchangeably to refer to a male reproductive cell. According to the present disclosure, the term semen, semen sample, and the like, have the standard meaning used in the art. That is, semen is male reproductive fluid comprising spermatozoa and fluid from the seminal vesicles and fluid from the prostate gland and other reproductive glands.

In various embodiments of the invention, the ORP characteristics of a biological sample of a subject are measured. The measurement of the ORP characteristics of a biological sample can be done at one or at multiple time points. The frequency of such measurements will depend on the condition being evaluated. For example, evaluation of the fertility of a male subject may require a single test. In contrast, evaluation of the fertility of a female subject, for example, may require periodic testing through an entire menstrual cycle. Similarly, determination of egg competence or sperm quality during a treatment phase may require periodic testing. As such, for example, testing can be done every 30 minutes, hour, 2 hours, 3 hours, 4 hours, 5 hours, 6 hours, 12 hours or 18 hours. Alternatively, testing can be done every day, 2 days, 3 days, 4 days, 5 days, 6 days, week, 2 weeks, 3 weeks, month, 2 months, 3 months, 4 months, 5 months, 6 months, 7 months, 8 months, 9 months, 10 months, 11 months, or year for more chronic conditions.

In various embodiments of the invention, the ORP characteristics of a biological sample of a subject are measured for purposes of evaluating sperm quality, evaluating ovum quality, evaluating fertility, selecting ovum, zygotes or embryos for implantation or monitoring a pregnancy following transfer of a fertilized egg (e.g., zygote, blastocyst, etc.) into a female. In such embodiments, the methods can also include identifying in the subject a risk factor, such as a lifestyle or genetic risk factor, for infertility.

Sperm Quality

An important aspect of successful conception is the quantity and quality of spermatozoa in a sample (e.g., a semen sample). Thus, current methods for evaluating fertility involve counting the number of sperm cells having normal motility (movement) and morphology (shape) and evaluation of the chemical and biochemical characteristics (e.g., pH, color, turbidity, liquefaction and viscosity) of the semen. However, it has also become apparent that the oxidative state of the semen affects the quality of the sperm. For example, it has been shown that oxidative stress is a major cause of DNA fragmentation (Wright, et al., Reprod Biomed Online 2014 June; (28(6):684-703); Saleh R A, et al. 2003 June; 7 Suppl 3:1597-605) and that such fragmentation is a major indicator of fertility potential, more so than even conventional semen parameters. Accordingly, reducing oxidative stress may improve sperm quality and consequently improve the chances for a successful conception. Thus, in one embodiment of the invention, the quality of sperm from an individual is determined by measuring the ORP characteristics of a sample from the individual and evaluating if the ORP characteristics are significantly different from the ORP characteristics of a reference ORP value. The ORP being measured can be sORP and/or cORP. Measured ORP values can also be used to determine an ORP/Concentration (ORP/Conc.) value (e.g., $mV/10^6$ sperm/mL). The fertility potential of the sample and/or individual are then determined from this comparison. In such a method, a significant increase in the ORP characteristics over the ORP characteristics from a sample known to have a high fertility potential indicates the sample, or individual, has a low fertility potential. Likewise, an ORP value similar to that of (about the same as) a sample known to have a low fertility potential indicates the sample being tested has a low fertility potential. As used herein, and with particular regard to spermatozoa, fertility potential refers to the ability of spermatozoa from an individual to fertilize an egg. Such fertilization potential can encompass any aspect of fertilization in which sperm are involved, such as transit of the sperm through the female reproductive tract, the ability of sperm to penetrate an egg into which it has come in contact, entry of the sperm cell into the egg and the initiation of cellular division. Sperm having high fertility potential are able to successfully transit the female reproductive tract, penetrate an egg and initiate the process of cellular division and embryo development. In preferred embodiments, the sample is a freshly collected sample.

As has been discussed, ORP can be used to determine the quality and fertility potential of a semen or seminal fluid sample. Sperm quality and fertility potential can be related to any spermatozoa characteristic known to be related to the ability of a sperm cell to fertilize an egg and initiate embryo development. Examples of such characteristics include, but are not limited to the viscosity of the ejaculate (i.e., semen), the ability of the ejaculate to liquefy, the total number of sperm cells in the ejaculate, the concentration of sperm cells in the ejaculate, the total motility of the sperm cells, the progressive motility of the sperm cells and the morphology of the sperm cells. Abnormal characteristics can be identified by the presence of increased ORP values. Thus, in one embodiment of the invention, the quality of sperm from an individual is determined by measuring the ORP characteristics of a sample from the individual and evaluating if the ORP characteristics are significantly different from the ORP characteristics of a reference ORP value. As used herein with regard to reference ORP values and cut-off values, the term significantly different, and the like, refers to a difference of at least 10%, at least 15% or at least 20%. If the reference ORP is a specific cut-off value, then any value when rounded, greater than the cut-off value is considered significant. For example, if the cut-off value is 1.0, a measured ORP value of 1.06 would round to 1.1 and would be considered significant. Moreover, a measured ORP value of 1.04 would round to 1.0 and would not be considered significant. In one embodiment, the fertility potential of sperm from an individual is determined by measuring the ORP characteristics of a sample from the individual and evaluating if the ORP characteristics are significantly different from the ORP characteristics of a reference ORP value. In one embodiment, if the measured ORP value is significantly higher than the reference ORP value, the sperm sample being tested is designated as having low fertility potential. In one embodiment, if the measured ORP value is about the same as the reference ORP value, the sperm sample being tested is designated as having a high fertility potential.

One embodiment of the invention is a method of determining if the number of sperm cells in a sample from a subject is within a normal range, (and therefore within a fertile range), the method comprising measuring the ORP characteristics of the sample, comparing the measured ORP value to one or more reference ORP values (e.g., a cut-off value) determined to be predictive of the number of sperm cells in a sample; using the results of the comparison to determine if the number of sperm cells in the measured sample is within the normal range. For example, an ORP value obtained from a semen or seminal fluid sample can be compared to an ORP cut-off value, or a range of ORP values, determined to be predictive of a normal number of sperm cells. If the measured value is about the same, or less than, the cut-off value, or is within, or about the same as, the range of ORP values determined to be predictive of a normal number of sperm cells, the sample being measured would be designated as having a normal number of sperm cells. Thus the sample would be considered fertile, or as having good fertility potential (good quality). If the measured ORP value is significantly greater the cut-off value, or is significantly outside the range of ORP values determined to be predictive of the normal number of sperm cells, the sample being measured would be designated as having an abnormal number (e.g., too few) of sperm cells. Thus the sample would be considered infertile, or as having poor fertility potential (poor quality).

One embodiment of the invention is a method of determining if the concentration of sperm cells in a sample from a subject is within a normal concentration range, (and therefore within a fertile concentration range), the method comprising measuring the ORP characteristics of the sample, comparing the measured ORP value to one or more reference ORP values (e.g., a cut-off value), determined to be predictive of sperm cell concentration; using the results of the comparison to determine if the concentration of sperm cells in the measured sample is within the normal range. For example, an ORP value obtained from a semen or seminal fluid sample can be compared to an ORP cut-off value, or a range of ORP values determined to be predictive of the normal concentration of sperm cells. If the measured value is about the same the cut-off value, or is within, or about the same as, the range of ORP values determined to be predictive of the normal concentration of sperm cells, the sample being measured is designated as having a normal concentration of sperm cells. Thus the sample would be considered fertile, or as having good fertility potential (good quality). If the measured ORP value is significantly greater than the cut-off value, or is significantly outside the range of ORP values determined to be predictive of the normal concentration of sperm cells, the sample being measured is designated as having an abnormal concentration of sperm cells. Thus the sample would be considered infertile, or as having poor fertility potential (poor quality).

One embodiment of the invention is a method of determining if a semen or seminal fluid sample has a normal percent of total motile sperm cells, (and therefore considered fertile), the method comprising measuring the ORP characteristics of the sample, comparing the measured ORP value to one or more reference ORP values (e.g., a cut-off value) determined to be predictive of the normal percent of total motile sperm cells; using the results of the comparison to determine if the percent of total motile sperm cells in the measured sample is within the normal range. For example, an ORP value obtained from a semen or seminal fluid sample can be compared to an ORP cut-off value, or a range of ORP values determined to be predictive of the normal percent of total motile sperm cells. If the measured value is about the same, or less than, the cut-off value, or is within, or about the same as, the range of ORP values determined to be predictive of a sample having a normal percent of total motile sperm cells, the sample being measured is designated as having a normal percentage of total motile sperm cells. Thus the sample would be considered fertile, or as having good fertility potential (good quality). If the measured ORP value is significantly greater than the cut-off value, or is significantly outside the range of ORP values determined to be predictive of a sample having a normal percentage of total motile sperm cells, the sample being measured is designated as having an abnormal percentage (e.g., too few) of total motile sperm cells. Thus the sample would be considered infertile, or as having poor fertility potential (poor quality).

One embodiment of the invention is a method of determining if a semen or seminal fluid sample has a normal percent of progressively motile sperm cells, (and therefore considered fertile), the method comprising measuring the ORP characteristics of the sample, comparing the measured ORP value to one or more reference ORP values (e.g., a cut-off value) determined to be predictive of a sample having a normal percent of progressively motile sperm cells; using the results of the comparison to determine if the percent of progressively motile sperm cells in the measured sample is within the normal range. For example, an ORP value obtained from a semen or seminal fluid sample can be compared to an ORP cut-off value, or a range of ORP values determined to be predictive of a sample having a normal percent of progressively motile sperm cells. If the measured value is about the same, or less than, the cut-off value, or is within, or about the same as, the range of ORP values determined to be predictive of a sample having a normal percent of progressively motile sperm cells, the sample being measured is designated as having a normal percentage of progressively motile sperm cells. Thus the sample would be considered fertile, or as having good fertility potential (good quality). If the measured ORP value is significantly than the cut-off value, or is significantly outside the range of ORP values determined to be predictive of a sample having a normal percentage of progressively motile sperm cells, the sample being measured is designated as having an abnormal percentage (e.g., too few) of progressively motile sperm cells. Thus the sample would be considered infertile, or as having poor fertility potential (poor quality).

One embodiment of the invention is a method of determining if a semen or seminal fluid sample has a normal percent of sperm cells having a healthy morphology, (and therefore considered fertile), the method comprising measuring the ORP characteristics of the sample, comparing the measured ORP value to one or more reference ORP values (e.g., a cut-off value) determined to be predictive of a sample in which a normal percent of sperm cells have a healthy morphology; using the results of the comparison to determine if the percent of sperm cells having a healthy morphology in the measured sample is within the normal range. For example, an ORP value obtained from a semen or seminal fluid sample can be compared to an ORP cut-off value, or a range of ORP values determined to be predictive of a sample in which a normal percent of sperm cells have a healthy morphology. If the measured value is about the same, or less than, the cut-off value, or is within, or about the same as, the range of ORP values determined to be predictive of a sample in which a normal percent of sperm cells have a healthy morphology, the sample being measured is designated as having a normal percent of sperm cells having a healthy morphology. Thus the sample would be considered fertile, or as having good fertility potential (good quality). If the measured ORP value is significantly greater than the cut-off value, or is significantly outside the range of ORP values determined to be predictive of a sample in which a normal percent of sperm cells have a healthy morphology, the sample being measured is designated as having an abnormal percentage (e.g., too few) of sperm cells having a healthy morphology. Thus the sample would be considered infertile, or as having poor fertility potential (poor quality). As used herein, the term healthy morphology refers to a sperm cell having the appropriate physical characteristics such that the sperm is able to fertilize an egg. Examples of such characteristics include, but are not limited to the smoothness of the spermatozoa head, the shape of the spermatozoa head, the size of the spermatozoa head, the size and definition of the acrosome, the presence or absence of vacuoles in the head or tail, the length of the tail, the presence of absence of tail defects (e.g., split or bifurcated tails) and the ability of the tail to adequately propel the spermatozoa forward. Appropriate physical characteristics allowing a sperm cell to fertilize an egg are known to those skilled in the art.

As noted above, methods disclosed herein are useful for discriminating between sperm samples having high fertility potential and samples having low fertility potential. Consequently, methods of the present invention are also useful for determining if additional steps or treatments would be required for a sample to successfully fertilize an egg. Thus, in certain embodiments, following determination that a sample has good fertility potential, the sample, or subject, can be designated as not requiring further treatments in order for the sample, or the subject, to successfully fertilize an egg. In certain embodiments, following determination that a sample has poor fertility potential (due to, for example, too few sperm cells, too low a concentration of sperm cells, poor motility, poor unhealthy or abnormal morphology, etc.), the sample, or the subject from which the sample was obtained, can be designated as requiring further processing or treatment in order to successfully fertilize an egg. Such designation can be made by a medical professional (e.g., doctor, physicians assistant, nurse practitioner, or a laboratory technician) or it can be determined by a device, such as a computer that, following determination of, or receipt of, the results of the comparison, is programmed to determine (associate the results of the comparison with) a useful process or course of treatment. Useful processes and methods of treatment for increasing the likelihood of successful fertilization are known to those skilled in the art. In certain embodiments, the individual, or any institution with which the individual is related (e.g., hospital, clinic, doctors office, etc.), making, or reporting the results of, the determination to the subject (e.g., patient) can also administer the useful process of course of treatment. In certain embodiment, the individual, or any institution with which the individual is related (e.g., hospital, clinic, doctors office, etc.), can refer the sample, or subject (e.g., patient), to a second party or institution (e.g. fertility clinic) for further processing or treatment. One embodiment of the present invention is a system for determining the ability of a sperm sample from a subject to fertilize an egg, the system comprising:

a first device of the present invention for measuring the ORP value of a sample of the present invention;

a second device comprising a set of computer instructions stored on computer readable medium, and a central processing unit (CPU) the computer instructions being executable by the CPU, wherein the first device is capable of receiving the ORP value from the first device, and wherein upon receipt the ORP value from the first device, the second device determines the quality, or fertility potential, of the sample. In one embodiment, the first and second devices are physically connected by an electrical component capable of transferring the measured ORP value from the first device to the second device. In certain embodiments, the electrical component is a wire, cable, or bus. In one embodiment, the determination of quality, or fertility potential is made by a comparison of the measured ORP value with a cut-off ORP value, or range of ORP values, as has been disclosed herein, stored in the first or second device. In a further embodiment, following determination of the quality, or fertility potential, of the sample, the second device determines, and optionally outputs, a useful process or treatment for increasing the quality, or fertility potential, of the sample or subject.

According to the present disclosure, a reference ORP value, or range of values, can be any sORP value, or range of values, for which the associated quality, fertility potential, and/or other specific characteristics (e.g., sperm cell numbers, sperm cell concentration, motility, morphology) has been empirically determined. Thus, for example, a reference sORP value, or range of values, can be from a sample having poor quality, a low fertility potential, low sperm cell numbers, low sperm cell concentration, a low percentage of sperm cells having normal motility or a low percentage of sperm cells having normal morphology. Alternatively, the reference sORP value, or range of values, can be from a sample having high quality, a high fertility potential, a normal number of sperm cell, a normal concentration of sperm cells, a normal percentage of sperm cells having normal motility or a normal percentage of sperm cells having normal morphology. The reference value can be obtained simultaneously with the sORP value of the sample being tested or it can be a historical reference sORP value (i.e., obtained from previous collection of clinical and/or experimental data). Those skilled in the art are capable of identifying and applying the appropriate reference sORP value.

One example of a reference sORP is a cut-off value capable of differentiating fertile sperm (those samples achieving normal values on all semen parameters) from non-fertile sperm (those failing one or more parameters). While not intending to limit the invention to specific disclosure, one example of such a cut-off value is disclosed herein. Thus, one embodiment of the invention is a method for determining if a sperm sample is fertile or infertile, the method comprising determining the sORP, or sORP/Conc., of the sample, and comparing the measured sORP, or sORP/Conc., value, to a cut-off value. In one embodiment, the cut-off value is about 1.635 mV/$10^6$ cells/mL. It will be appreciated by those skilled in the art that such clinical values may vary slightly on a test to test or day to day basis. Thus, with regard to the term "about", those skilled in the art will be able to determine how much variation is encompassed by the term about. In general, such variation is 1%, 2%, 3%, 4% or 5%. In one embodiment, a sperm sample having a sORP/Concentration value less than about 1.635 mV/$10^6$ cells/mL is identified as being fertile. In one embodiment, a sperm sample having a sORP/Concentration value greater than about 1.635 mV/$10^6$ cells/mL is identified as being infertile.

A second example of a reference sORP is a cut-off value capable of differentiating semen with normal sperm morphology from those with abnormal sperm morphology. While not intending to limit the invention to specific disclosure, one example of such a cut-off value is disclosed herein. Thus, one embodiment of the invention is a method for determining if a semen sample has sperm with normal morphology from those with abnormal morphology, the method comprising determining the sORP, or sORP/Conc., of the sample, and comparing the measured sORP, or sORP/Conc., value, to a cut-off value. In one embodiment, the cut-off value is about 3.29 mV/$10^6$ sperm/mL. It will be appreciated by those skilled in the art that such clinical values may vary slightly on a test to test or day to day basis. Thus, with regard to the term "about", those skilled in the art will be able to determine how much variation is encompassed by the term about. In general, such variation is 1%, 2%, 3%, 4% or 5%. In one embodiment, a sperm sample having a sORP value less than about 3.29 mV/$10^6$ sperm/mL is identified as having a normal sperm morphology. In one embodiment, a sperm sample having a sORP value greater than about 3.29 mV/$10^6$ sperm/mL is identified as abnormal sperm morphology.

The sORP characteristics of the individual may be obtained from any biological sample of the subject, including but not limited to blood, plasma, serum, saliva, CSF, urine, penile secretions (including penile swabs), semen, seminal fluid (e.g., semen minus spermatozoa) or prostatic fluid, in a convenient and timely manner. The sORP of the subject may also be obtained from a tissue of the subject. In an embodiment where the sample is semen, the sample can, but need not, be subjected to further processing, such as, removal of spermatozoa, leaving the seminal plasma. In one embodiment, spermatozoa can be separated from semen and the ORP of the separated cells determined.

In order to determine the trend of sORP characteristics in an individual over time, without limitation, the ORP characteristics of the individual may be checked at suitable intervals, limited only by the physical restraints of generating a biological sample. For example, ORP characteristics can be checked every day, 2 days, 3 days, 4 days, 5 days, 6 days, week, 2 weeks, 3 weeks, month, 2 months, 3 months, 4 months, 5 months, 6 months, 7 months, 8 months, 9 months, 10 months, 11 months, or year.

The individual being tested may have already been determined as being infertile, as determined using standard definitions in the relevant field. Alternatively, the fertility status of the individual prior to testing may be unknown.

In a related embodiment, the sperm sample being analyzed for its fertility potential can be a stored sample. Such samples are well known in the field of reproductive biology. Moreover, it is appreciated that spermatozoa are usually cryogenically preserved and that such storage involves the use of cryoprotectant agents, such as glycerol and dimethyl sulfoxide. Recent evidence suggests that different cryoprotectants have different effects on the immediate environment of the stored spermatazoa and that the storage environment can affect the fertility potential of the stored sample. Thus, in one embodiment the sORP characteristics of a stored sample of spermatozoa are determined in order to assess the fertility potential of the sperm in the sample. The sample can be a semen sample or it can be a semen sample that has been further processed (e.g., centrifugation, washing, addition of buffers, cryoprotective agents, antioxidants, and the like) prior to storage. In one embodiment, the sORP characteristics are used to measure the effect of various storage conditions on sperm viability and/or fertility potential. In certain embodiments, the storage conditions are varied by the addition of antioxidants, such as for example, ascorbic acid and α-tocopherol.

Egg Quality

While sperm quality is important for successful fertilization (conception), equally as important is the quality of the egg being fertilized. Egg quality refers to physical characteristics of an egg (ovum) and its relationship to the ability to be fertilized and establish and maintain a successful pregnancy. As used herein, a successful pregnancy refers to a pregnancy that lasts long enough for the fetus to be capable of surviving outside of the mother's uterus. Currently, egg quality is determined by visual inspection of oocytes collected by transvaginal oocyte retrieval, which involves injections of hormones that cause the ovaries to ripen and release multiple eggs. The afore-mentioned visual inspection includes such things as the uniformity and thickness of the zona pellucid, color and uniformity of the ooplasm and degree of vacuolization (presence or absence of vacuoles). However, it is appreciated in the field that the oxidative status of the ovum, and its environment, can impact the ability of the ovum to be fertilized and establish and maintain a successful pregnancy. (see, for example, Agarwal, *Reproductive Biology and Endocrinology* 2005, 3:28) Thus, in one embodiment of the invention, the competence of an egg from an individual is determined by measuring the ORP characteristics of a sample from the individual and evaluating if the ORP characteristics are significantly different from the ORP characteristics of a reference ORP value. The competency of the egg and/or individual are then determined from this comparison. In such a method, an increase in the ORP characteristics over the ORP characteristics from a sample known to have high competency indicates the sample, or individual, has a low probability of being fertilized or of establishing or maintaining a pregnancy. Likewise, ORP characteristics similar to the ORP characteristics from a sample known to have low competency indicates the sample being tested, or individual, has a low probability of being fertilized or of establishing or maintaining a pregnancy. Moreover, ORP characteristics similar to the ORP characteristics from a sample known to have high competency indicates the sample being tested, or individual, has a high probability of being fertilized or of establishing or maintaining a pregnancy.

According to the present invention, competency refers to the ability of an egg to become fertilized, or to establish and maintain a viable pregnancy. As such, a competent egg is able to be fertilized by spermatozoa, is able to divide appropriately, maintain a diploid state, successfully implant in the endometrium of the uterus and proceed to at least the fetal stage of development. By contrast, an egg that is incompetent is unable to complete at least one of the above-listed steps. Fertilization of incompetent eggs often results in spontaneous termination of pregnancy prior to the fetal stage of development.

The ORP characteristics of the individual may be obtained from a biological sample of the subject, including but not limited to blood, plasma, serum, saliva, CSF, urine, vaginal secretions or follicular fluid, in a convenient and timely manner. The ORP of the subject may also be obtained from a tissue of the subject.

It will be appreciated by those skilled in the art that that, in certain circumstances (e.g., IVF), an oocyte can be cultured prior to further use. Thus, in certain embodiments, the sample from which the ORP is obtained can be medium in which the oocyte is cultured. In such embodiments, the ORP of the medium can be determined prior to, during and after a specified time of culture, and the ORP compared to an appropriate reference value. In such embodiments, an increase in the ORP characteristics of the medium relative to the ORP characteristics from a sample known to have high competency indicates the egg has a low probability of being fertilized or of establishing or maintaining a pregnancy.

In a related embodiment, the medium being tested can come from an egg that was cryogenically stored, thawed and cultured. Such samples are well known in the field of reproductive biology. Moreover, it is appreciated that cryogenic storage involves the use of cryoprotectant agents, such as glycerol and dimethyl sulfoxide. Recent evidence suggests that certain cryoprotectants may affect stored cells. Thus, methods of the present invention can also be used to determine the affect of storage on egg competence and to identify useful methods and compositions for such storage. In one embodiment, the ORP characteristics are used to measure the effect of various storage conditions on egg competence. In certain embodiments, the storage conditions are varied by the addition of antioxidants, such as for example, ascorbic acid and α-tocopherol.

In order to determine the trend of ORP characteristics in an individual over time, without limitation, the ORP characteristics of the individual may be checked at suitable intervals. For example, ORP characteristics can be checked every 30 minutes, hour, 2 hours, 3 hours, 4 hours, 5 hours, 6 hours, 12 hours or 18 hours. Alternatively, testing can be done every day, 2 days, 3 days, 4 days, 5 days, 6 days, week, 2 weeks, 3 weeks, month, 2 months, 3 months, 4 months, 5 months, 6 months, 7 months, 8 months, 9 months, 10 months, 11 months, or year.

The individual may have already been determined as being infertile, as determined using standard definitions in the relevant field. Likewise, the competency of eggs from an individual can already have been determined using other methods. Alternatively, the fertility status of the individual, or the competency of individual's eggs, may be unknown prior to testing.

Fertility/Treatment of Infertility

A reduction in sperm quality or egg quality can be manifest as an overall reduction in an individual's fertility. Such a reduction can be sub-fertility or infertility. One embodiment of the invention is a method to identify an individual that has reduced fertility, the method comprising measuring the ORP characteristics of a sample from the individual and evaluating if the ORP characteristics are significantly different from the ORP characteristics of a reference ORP value. The fertility potential of the individual is then determined from this comparison. In such a method, an increase in ORP over the ORP from a sample from an individual known to be fertile indicates the individual being tested has reduced fertility.

As used herein, sub-fertile refers to an individual having a condition making conception less likely, but not impossible. Thus, sub-fertility refers to any form of reduced fertility having a prolonged time of unwanted non-conception. For example, women having polycystic ovary syndrome (PCOS), in which reproductive hormones are out of balance relative to a woman not having PCOS, are considered sub-fertile. Such women can get pregnant; however, it usually takes longer than women who do not have PCOS. As used herein, the term infertile refers to an individual who is unable to achieve a successful pregnancy after 12 months of unprotected intercourse. Such terminology is understood by those in the field of reproductive medicine.

Sub-fertility and infertile can result due to a variety of factors. As discussed above, sub-fertility or infertility can be due to sperm or eggs of poor quality. However, other factors may also affect fertility. For example, in men, reasons for sub-fertility or infertility include, but are not limited to, infections, hormonal problems in the pituitary gland or the testicles, testicular injury or failure, hematospermia, cancer treatments (e.g., chemotherapy, radiation, etc.), antibodies against sperm (e.g., following vasectomy or injury) or drug use (e.g., tobacco, marijuana, etc.). In women, reasons for sub-fertility or infertility include, but are not limited to, infections, scarring of uterus or fallopian tubes, endometriosis, cysts, fibroids, damage to the cervix or uterus (for example, following surgery such as D&C), hormonal problems, abnormalities in cervical mucus, antibodies to sperm, cancer treatment, thyroid problems, stress or drug use (e.g., tobacco, marijuana, etc.)

It will be understood by those in the field that the terms sub-fertile and infertile are clinical definitions based on time to conception. Consequently, such diagnoses may be different points on a relative scale. For example, an individual, or couple, diagnosed as sub-fertile may later be diagnosed as infertile. Alternatively, an individual, or couple, diagnosed as infertile may later be found to be sub-fertile. Consequently, those skilled in the art will understand that the corresponding changes in ORP will also be of varying degree. For example, it is expected that samples from sub-fertile individuals will have an elevated ORP compared to the ORP in a sample from a fertile individual. It is further expected that the ORP of a sample from an infertile individual will not only be higher than that observed in a fertile individual, but may also be higher than that observed in a sub-fertile individual. Thus, it will be apparent that in certain embodiments, the degree of increase of the ORP value is a direct inverse correlate to the level of fertility. Consequently is important that the determined ORP value is compared to a well-established set of historic ORP values corresponding to fertile, sub-fertile and infertile individuals.

Methods of the present invention can also be used to determine the likelihood of an individual to be able to achieve conception (i.e., fertilization of an egg). Such information is useful in determining the need for medical assistance in achieving conception. Thus, one embodiment of the present invention is a method for determining the likelihood of an individual being able to conceive, the method comprising measuring the ORP characteristics of a sample from the individual and evaluating if the ORP characteristics are significantly different from the ORP characteristics of a reference ORP value. The likelihood of the individual being able to conceive are then determined from this comparison. In such a method, an increase in the ORP characteristics over the ORP characteristics from an individual, or pool of individuals, known to be able to conceive without medical intervention indicates the individual, has a low probability of being able to conceive and maintain a pregnancy. Thus, such information is invaluable in determining the need for medical assistance in achieving pregnancy. One embodiment is a method of identifying an individual that would benefit from medical assistance with regard to conceiving a child, the method comprising measuring the ORP characteristics of a sample from the individual and evaluating if the ORP characteristics are significantly different from the ORP characteristics of a reference ORP value. The likelihood of the individual benefiting from medical assistance with regard to conception are then determined from this comparison. In such a method, an increase in the ORP characteristics over the ORP characteristics from an individual, or pool of individuals, known to be able to conceive a child without medical intervention indicates the individual would benefit from medical assistance with regard to conception and maintenance of a pregnancy. In contrast, an ORP characteristic similar to an ORP characteristic in a sample from an individual known to be able to conceive without medical assistance indicates the individual being tested would be unlikely to benefit from medical assistance.

One embodiment of the invention is a method for determining a treatment plan for achieving pregnancy, the method comprising measuring the ORP characteristics of a sample from the individual and evaluating if the ORP characteristics are significantly different from the ORP characteristics of a reference ORP value. In such a method, if the ORP value is substantially the same as the value observed in a sample from an individual, or pool of individuals, known to be able to conceive without medical assistance, the individual being tested is diagnosed as unlikely to benefit from treatment for reduced fertility. Alternatively, if the ORP value of the sample being tested is significantly higher than the ORP value from a sample from an individual, or pool of individuals, known to be able to conceive without medical assistance, the individual being tested is diagnosed as likely to benefit from treatment for reduced fertility.

It is known in the art that methods exist for the treatment of infertility in individuals. For example, it is appreciated in the field that poor sperm quality can be improved by, for example, the ingestion of antioxidants such as reservatrol or ascorbic acid. Thus, in one embodiment, the efficacy of treating sperm quality, sub-fertility and/or infertility in an individual is monitored by measuring the ORP characteristics of a sample from an individual. Measurement of ORP characteristics in such an embodiment can be obtained prior to treatment and at suitable intervals during and following treatment. In such an embodiment, it would be expected that treatment resulting in an improved sperm quality would also result in a decrease in ORP value. Consequently, failure of a treatment to reduce the ORP value, or an increase in the ORP value, would indicate the treatment is not effective and should be re-evaluated. Such re-evaluation includes, for example, an increase in dosage, discontinuation of the treatment, and/or administration of a new or adjuvant treatment.

In-Vitro Fertilization (IVF)

Heretofore has been described use of methods of the present invention for the evaluation of sperm quality, egg quality and general fertility. It should be apparent to those skilled in the art that such methods can also be used in specific applications relating to in vitro fertilization. In the process of in vitro fertilization, the ovary is stimulated with hormones such that more than one egg matures and is released. The released eggs (oocytes) are collected, maintained in culture medium and the most promising (i.e., most competent) are fertilized by contacting them with sperm obtained from a collected sample. The fertilized eggs (zygotes) are then typically cultured for another 2 (cleavage stage) to 5 (blastocyst stage) days at which time the most promising zygotes (or blastocysts) are transferred to the recipient's uterus, where the implant and continue to grow. From this brief description, it can be seen that, in addition to assessing the quality of sperm, there are several other points in the IVF process at which methods of the present invention can be employed. For example, as has been previously described, methods of the present invention can be used to determine the competency of collected eggs.

One embodiment of the present invention is a method for assessing the quality of a fertilized egg, the method comprising measuring the ORP characteristics of a sample of the medium in which the fertilized egg is cultured and evaluating if the ORP characteristics are significantly different from the ORP characteristics of a reference ORP value. The quality of the fertilized egg is then determined from this comparison. In such a method, an increase in the ORP characteristics over the ORP characteristics from a sample from an egg known to have high quality indicates the fertilized egg being tested has a low quality and is unlikely to establish or maintain a successful pregnancy. Likewise, ORP characteristics similar to the ORP characteristics from a sample from a fertilized egg known to have a low quality indicates the fertilized egg being tested is unlikely to establish or maintain a successful pregnancy. In contrast, ORP characteristics similar to the ORP characteristics from a sample from a fertilized egg known to have a high quality indicates the fertilized egg being tested is likely to establish and maintain a successful pregnancy. In one embodiment, the fertilized egg being tested is a zygote. In one embodiment, the fertilized egg is a blastocyst.

In order to determine the trend of ORP characteristics in a cultured egg over time, without limitation, the ORP characteristics of the culture medium may be checked at suitable intervals. For example, ORP characteristics can be checked every 30 minutes, hour, 2 hours, 3 hours, 4 hours, 5 hours, 6 hours, 12 hours or 18 hours. Alternatively, testing can be done every day, every 2 days or every 3 days.

One embodiment of the present invention is a method of improving the likelihood a fertilized egg will achieve a successful pregnancy, the method comprising measuring the ORP characteristics of a sample of the medium in which the fertilized egg is cultured, evaluating if the ORP characteristics are significantly different from the ORP characteristics of a reference ORP value, and if the ORP characteristics are significantly different from the ORP characteristics of a reference ORP value, treating the culture medium to improve the ORP characteristics of the fertilized egg. In such embodiments, treatment of the cultured fertilized egg can comprise treating the culture medium (e.g., with antioxidants) to improve the ORP characteristics of the medium, or treating the egg with a pharmaceutical compound to improve the quality of the egg.

Because a decrease in egg quality can reduce the chances that a fertilized egg will establish and maintain a successful pregnancy, methods of the present invention can be used to improve the chances that a fertilized egg will establish a successful pregnancy. Thus, one embodiment of the present invention is a method for improving the chances that a fertilized egg will establish a successful pregnancy, the method comprising measuring the ORP characteristics of a sample from the individual and evaluating if the ORP characteristics are significantly different from the ORP characteristics of a reference ORP value. The optimal time for transferring the fertilized is then determined from this comparison. In such a method, an increase in the ORP characteristics over a pre-determined ORP threshold value, or cut-off value, indicates it is time to transfer the fertilized egg into the uterus. The threshold ORP value represent an ORP value above which, the chance of establishing and maintaining a successful pregnancy, is significantly reduced compared to the chance of establishing and maintaining a successful pregnancy observed at the threshold, or lower, ORP values. The threshold ORP can be determined, for example, from historical ORP data obtained from previous successes or failures in transferring fertilized eggs.

Pregnancy/Fetal Health

Pregnancy is a prolonged state of oxidative stress arising from increased placental mitochondrial activity and production of reactive oxygen species. Excessive production of ROS may occur at certain windows in placental development and in pathologic pregnancies, such as those complicated by preeclampsia and/or IUGR, overpowering antioxidant defenses, with deleterious outcome. For example, in the first trimester, establishment of blood flow into the intervillous space is associated with a burst of oxidative stress. The inability to mount an effective antioxidant defense against this may result in early pregnancy loss. Oxidative stress peaks by the second trimester of pregnancy, ending what appears to be a vulnerable period for fetal health and gestational progress. In late gestation, increased oxidative stress may be seen in pregnancies complicated by diabetes, IUGR, and preeclampsia.

Another embodiment of this invention is a method of diagnosing, evaluating and/or monitoring pregnancy in a subject as well as monitoring progress in fetal development or risk by measuring the ORP characteristics of a biological sample from such a subject and then evaluating if the ORP characteristics are significantly different than the ORP characteristics of a reference value, such as a biological sample from a non-pregnant population or from a pregnant population to determine the pregnancy and/or fetal development status of the subject. The subject is then treated based on the pregnancy and/or fetal development status. In these methods, an increase in the ORP characteristics of the subject over the ORP characteristics of non-pregnant subjects is indicative of the presence of pregnancy in the subject. Alternatively, or in addition, an increase in the ORP characteristics of the subject over the ORP characteristics of a reference value from pregnant subjects known to have normal pregnancy of the same gestational period, is indicative of a potential developing maternal or fetal risk or high-risk pregnancy in the subject.

In order to determine the trend of the ORP characteristics in such subjects over time, without limitation, the ORP characteristics value of the subject may be checked every 1, 2, 3, 4, 5, or 6 days or weeks after the initial determination in order to compare and determine a trend in the ORP characteristics value of the subject.

The ORP characteristics of the subject may be obtained from a body fluid of the subject, including but not limited to blood, plasma, amniotic fluids, and serum. The ORP characteristics of the subject may also be obtained from a tissue of the subject, including but not limited to, placental or fetal tissues.

Thus, in one embodiment, a pregnant subject may be evaluated for ORP characteristics values indicative of abnormal pregnancy or increased fetal risk in the subject. An ORP characteristics value of the subject that is statistically similar to, or less than, the ORP characteristics value from subjects known to have a normal pregnancy of the same gestational period is indicative of a subject that is progressing with normal pregnancy. An ORP characteristics value of the subject that is statistically similar to, or greater than, the ORP characteristics value from subjects known to have a normal pregnancy of the same gestational period is indicative of a subject that is not progressing to normal pregnancy or may be progressing to abnormal pregnancy, including preeclampsia or eclampsia, gestational diabetes, or may be at elevated risk of miscarriage or fetal death.

The ORP characteristics values of such subject may be checked regularly after the initial determination in order to re-evaluate the initial evaluation of normal pregnancy or abnormal pregnancy or fetal development or developmental progression. In a related embodiment, a pregnant subject may be regularly monitored by evaluation of the subject's ORP characteristics values compared with ORP characteristics values indicative of normal fetal development. An ORP characteristics value of the subject that is progressing statistically to an ORP characteristics value that is similar to, or greater than, the ORP characteristics value from subjects having a normal pregnancy compared with the subject, is indicative of a subject that may be progressing to unhealthy or abnormal pregnancy.

The ORP characteristics values of such subject may be checked, without limitation, every 1, 2, 3, 4, 5, or 6 weeks or every 1, 2, 3, 4, 5, or 6 months after the initial determination in order to evaluate the subject's pregnancy progress and/or disease prognosis.

In some embodiments, subjects found to have elevated ORP characteristics indicative of abnormal or high-risk pregnancy are administered an antioxidant regimen and/or a regimen of avoidance of iron excess to ameliorate maternal and early fetal damage.

While the aforementioned methods have focused on determining ORP characteristics, in certain embodiments, the ORP characteristics measurement is taken along with other patient diagnostic criteria such as, for example, one or more of vital signs, ECG, blood sugar level, CT scan (CAT Scan, Computed axial tomography), MRI (Magnetic resonance imaging, MR), MRA (Magnetic resonance angiogram), Cerebral arteriogram (Cerebral angiogram, Digital subtraction angiography), PT (Prothrombin time) or PTT (Partial thromboplastin time. Additionally, the ORP characteristics measurement may be used alone or in conjunction with the other diagnostic criteria described above to evaluate the use of various therapies of interventions.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1. Establishment of Oxidation-Reduction Potential in Semen and Seminal Plasma This Example demonstrates that ORP can be measured in semen and seminal plasma samples.

Male partners from couples concerned about infertility were recruited from a single international andrology laboratory (Clinical Studies) or from a national urology laboratory (Technical Studies). A single semen sample was donated by each participant. Semen samples were allowed to liquefy at room temperature for approximately 30 minutes, following WHO guidelines (5th Edition, 2010) for liquefaction. Following liquefaction, the samples were divided into two fractions. One fraction was centrifuged at 300 g for seven minutes to isolate the seminal plasma.

Semen Analysis

Following liquefaction, ejaculate volume, sperm cell number, sperm concentration, morphology, total and progressive motility were measured using WHO guidelines for sperm quality (2010, 5$^{th}$ Edition). Smears were stained with a Diff-Quik kit for assessment of sperm morphology. Samples were also tested for Leukocytospermia, i.e. >1×10$^6$ WBC/mL when the round cell concentration was >1×10$^6$ and confirmed by the peroxidase or the Endtz test. Sperm count and motility were assessed manually.

Oxidation-Reduction (ORP) Measurement sORP (mV/10$^6$ sperm/mL) was measured in both fractions using the RedoxSYS test comprised of a Redox SYS analyzer MiOXSYS (Aytu Biosience) sensor (MiOXSYS, Aytu BioScience). The sensor was inserted face-up and with the sensor electrodes facing the MiOXSYS Analyzer. Using a micropipette, 30 μL of sample (semen or seminal plasma) was released onto the sensor's application port. Once the sample reached the reference cell of the sensor, the testing automatically began and audible beeps indicated completion of the test. The sORP (in millivolts or mV) was recorded. Analysis was performed in triplicate and the average values were corrected for sperm concentrations and expressed as sORP (mV/10$^6$ sperm). Values are reported as mean±SEM. Spearman correlation and Receiver Operating Characteristic curves (ROC) were used for statistical analysis.

Statistical Analysis

Spearman correlation test was used for statistical analysis to compare qualitative variables. A P value of <0.05 was considered statistically significant.

Figure 7:
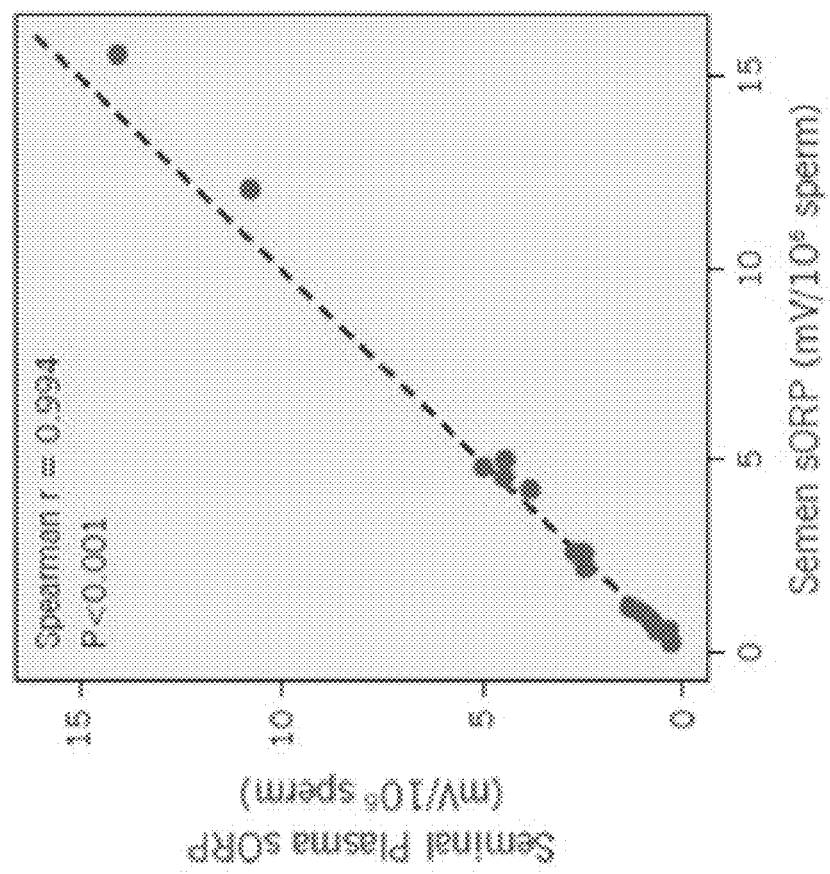
FIG. 7 shows a comparison between the sORP values measured from samples tested as semen (X axis) and again as seminal plasma (Y axis), based on sORP/Concentration ($mV/10^6$ sperm/mL).
Figure 8:
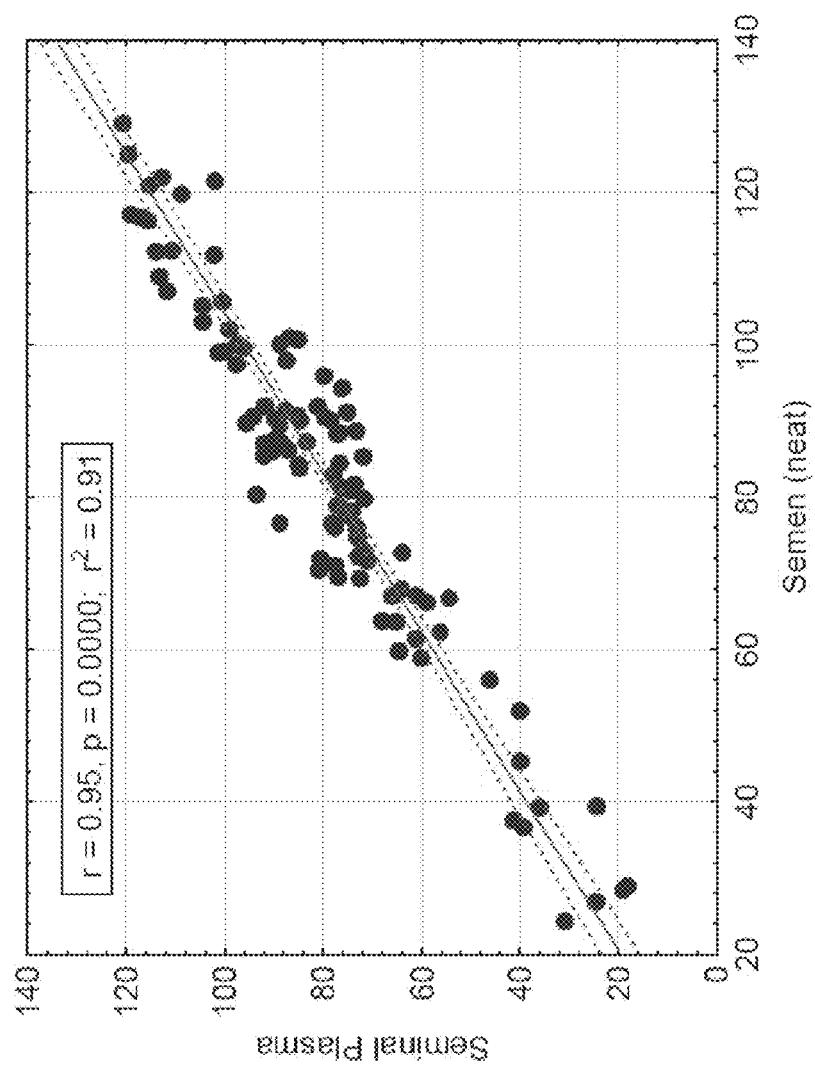
FIG. 8 shows a comparison between the raw sORP values (mV) of semen and seminal plasma.

The results of these analyses are shown in FIGS. 7 and 8. The results demonstrate that the MiOXSYS test can accurately measure ORP in semen and seminal plasma levels, and that the sORP values semen matched those measured in seminal plasma.

Figure 9:
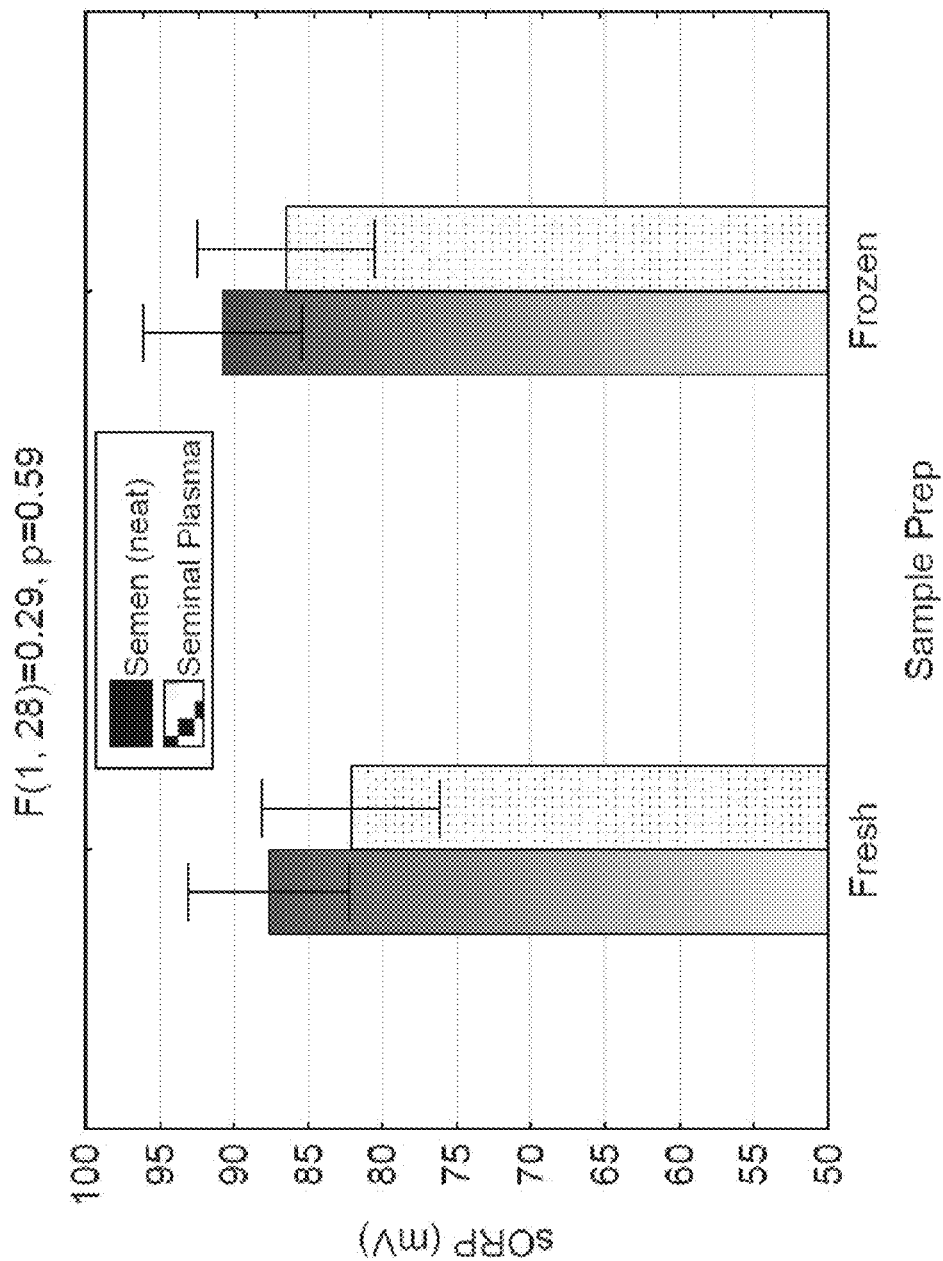
FIG. 9 illustrates the effect of freezing the sample on the sORP values of semen and seminal fluid.

Example 2. Comparison of sORP/Concentration Measures Using Fresh and Frozen Samples Semen samples were obtained and treated as described in Example 1. Samples were then stored at −80° C. for 120 minutes, after which they were thawed, brought to room temperature and sORP measured. The result of this analysis is shown in FIG. 9.

The results demonstrate freezing samples, either as semen or seminal plasma, does not alter the sORP value, and further confirms the lack of difference between semen and seminal plasma samples.

Figure 10:
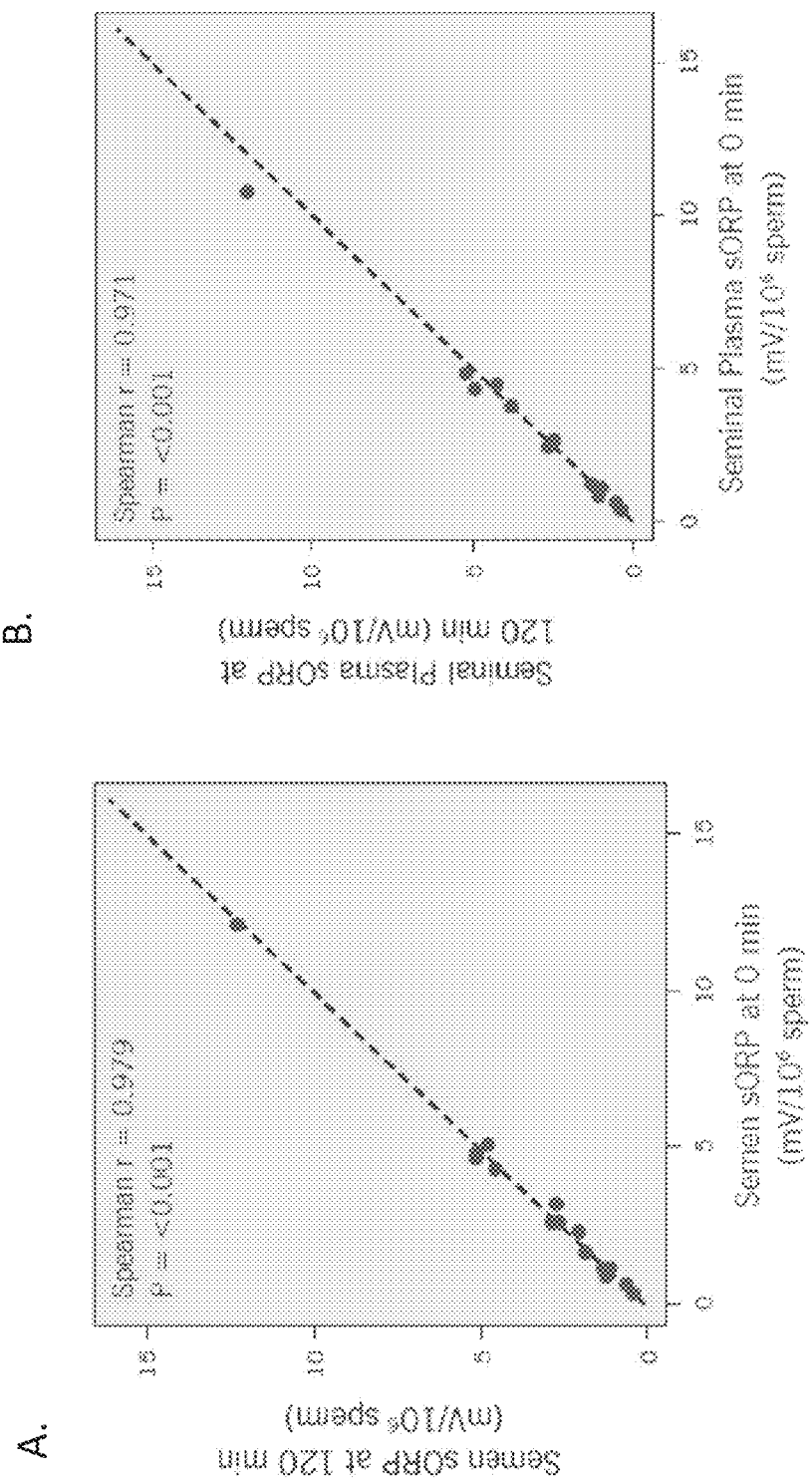
FIG. 10 illustrates the effect of time on sORP/Conc. value of semen (10A) and seminal plasma (10B). X axis is the sORP Conc. value of semen (10A) or seminal plasma (10B) at 0 minutes. Y axis is the sORP/Conc. value of semen (10A) or seminal plasma (10B) at 120 minutes.
Figure 11:
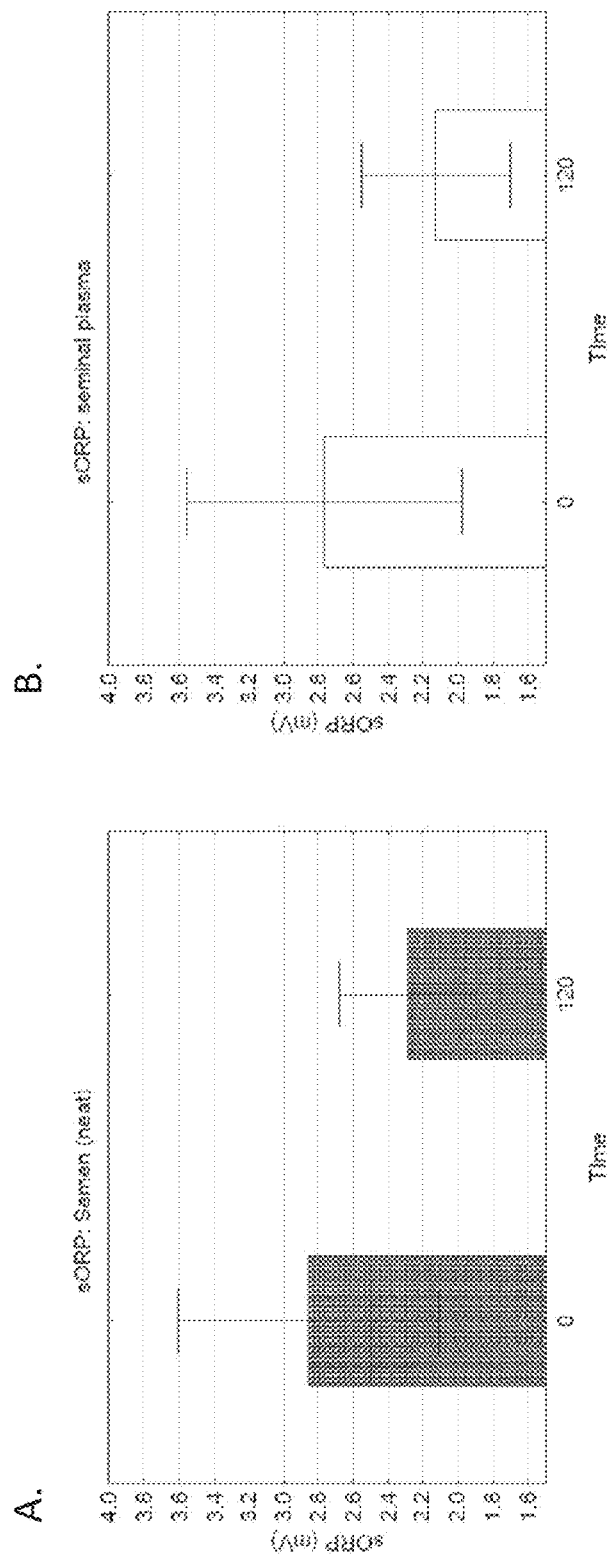
FIG. 11 illustrates the effect of time on sORP value (mV) of semen (10A) and seminal plasma (10B). Left bar in each graph is the sORP value (mV) at 0 minutes. Right bar in each graph is the sORP value (mV) at 120 minutes.

Example 3. Effect of Time on Oxidation-Reduction Potential in Semen and Seminal Plasma Semen samples were obtained and treated as described in Example 1. sORP was measured immediately after liquefaction (0 minutes). The samples were then left at room temperature for 120 minutes and retested (120 minutes). The results are shown in FIGS. 10 and 11.

The results demonstrate that there is no difference in sORP values in samples that were tested immediately and those which were measured at a later time point.

Figure 12:
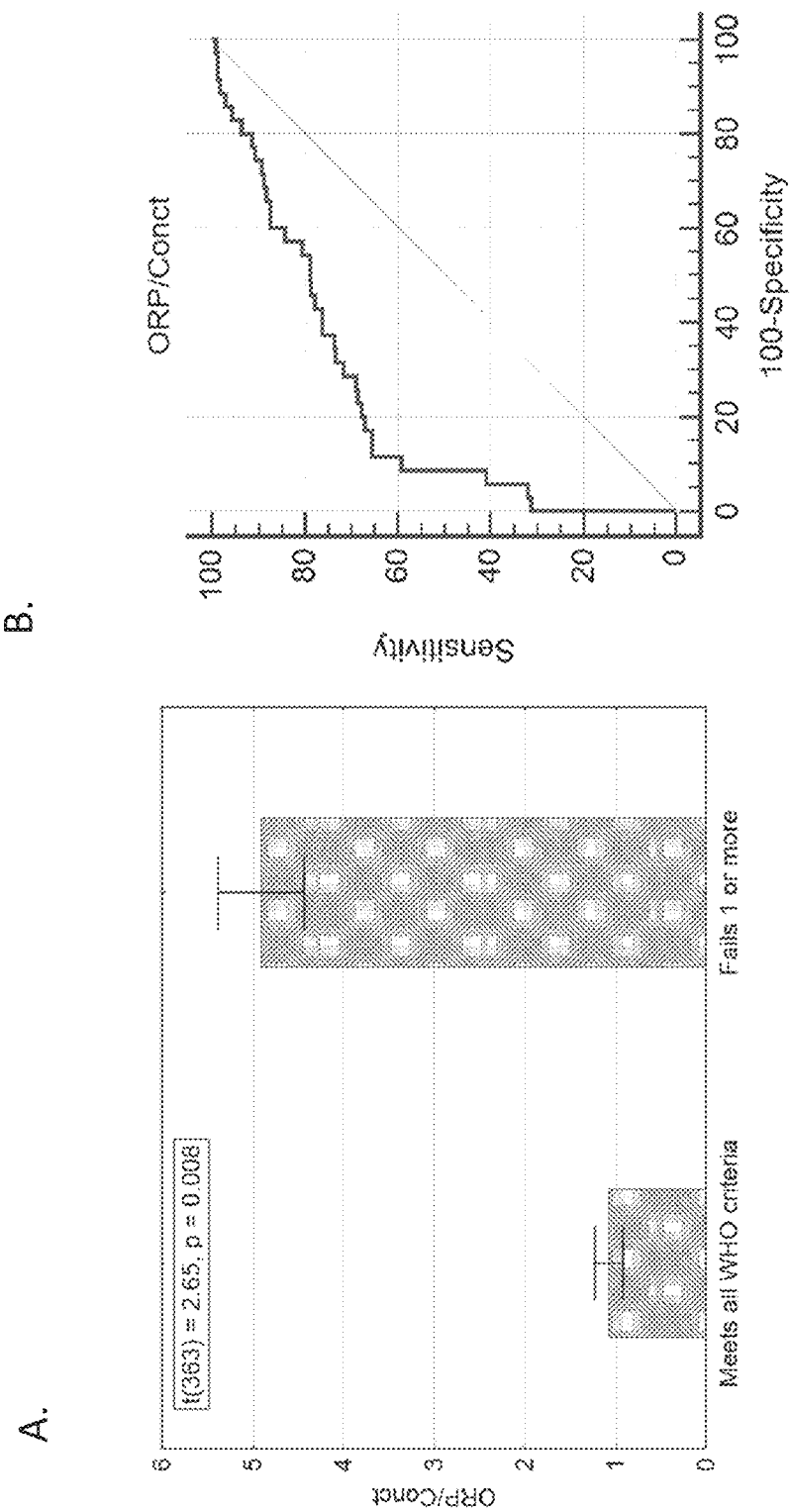
FIG. 12. Determination of sORP cut-off value for predicting fertility. A) shows a comparison of sORP/Conc. values from fertile (left bar) and infertile (right bar) samples, as determined according to WHO criteria for fertility. B) illustrates a receiver operating characteristic (ROC) analysis for identifying an sORP value that best separates fertile samples from infertile samples. The jagged line represents the sORP values associated with various levels of sensitivity (y-axis) and specificity (x-axis). Solid straight line represents the predictive ability based on statistical chance. The area between the two lines represents the AUC.

Example 4. sORP Cut-Off Value that Differentiates Fertile Sperm from Non-Fertile Sperm Samples from 398 participants, collected across three data sets, were analyzed for semen parameters as described in Example 1. 35 samples met all 6 criteria for fertile sperm according to the WHO Guidelines (5$^{th}$ Edition, 2010). 363 samples failed to meet one or more criteria, labeling them "infertile". The sORP/Conc. value of each sample was determined and the average sORP/Conc. values for fertile and infertile samples compared. The results of this comparison are shown in FIG. 12A. A receiver operating characteristic (ROC) analysis was used to identify a sORP criterion that best predicts the fertile samples from the infertile samples. The results of these analyses are shown in FIG. 12B and in Table 1 below.

TABLE 1

| sORP/Conc. cut-off value for fertility | |
|---|---|
| sORP Cut-Off Value for Fertility | >1.635 mV/10$^6$ cells/mL |
| Area Under the Curve (AUC, (95% CI)) | 0.78 (0.74-0.82)* |
| Sensitivity (95% CI) | 59.5 (54.2-64.5) |
| Specificity (95% CI) | 91.4 (76.9-98.2) |
| Positive Predictive Value (95% CI) | 98.6 (96.1-99.7) |
| Negative Predictive Value (95% CI) | 17.8 (12.5-24.2) |

*Significant at p < 0.05

The results demonstrate that sORP values (sORP/Concentration) were lower in the semen samples that met all WHO criteria for fertility compared to those that were infertile. The results also demonstrate that a cut-off value of 1.635 accurately identified 91.4% of all fertile samples. Thus, a semen sample with an sORP/Concentration value greater than 1.635 will be infertile with 98.6% confidence.

Example 5. sORP Values and Sperm Morphology

This Example demonstrates the identification of a sORP cut-off value for differentiating sperm having normal morphology from sperm having abnormal morphology.

Semen samples from males suspected of infertility were collected for a total of 400 participants. Inclusion criteria were males seeking fertility assessment. Exclusion criteria were males with azoospermic samples. A single semen sample was donated by each participant from which ejaculate volume, sperm cell number, sperm concentration, morphology, total and progressive motility were measured using the WHO guidelines (2010, 5$^{th}$ Edition) for sperm quality, which are shown in Table 2 below.

TABLE 2

Normal Semen Parameter References
(WHO, 5$^{th}$ Edition, 2010)

| Characteristic | Lowest normal limit | WHO guideline section reference |
|---|---|---|
| Volume (mL) | >1.5 mL | 2.3.4.1 |
| Total sperm # | >39 × 10$^6$ | 2.8.8 |
| Concentration (million cells/mL) | >15 × 10$^6$/mL | 2.8.6 |
| Total Motility | >40% | 2.5.4 |
| Progressive Motility | >32% | 2.5.4 |
| Morphology | >4% | 2.17.3 |

Specifically, cell numbers were quantified using a Makler chamber. Morphology was assessed using prepared slides by the Quik-Diff staining protocol.

sORP Measurements

Oxidative stress was assessed by measuring the static oxidation-reduction potential (sORP) of neat liquefied semen samples using the MiOXSYS™ System (Aytu Bioscience, Inc). The MiOXSYS System is comprised of the MiOXSYS analyzer and disposable test sensors. This is a galvanostatic measure of the electron transfer from reductants (antioxidants) to oxidants under a steady low voltage reducing current; thus it provides an aggregate measure of all current oxidant activity and antioxidant activity in a sample. Higher sOPR values (millivolts, mV) indicate a higher oxidant activity relative to the antioxidant activity; a greater state of oxidative stress.

Briefly, 30 μL of room temperature neat semen was added to a test sensor pre-inserted into the analyzer. Testing began automatically when the sample was detected at the sensor's reference electrodes. Each run was two minutes and samples were run in duplicate. If the duplicates differed by more than 10 mV, a third sample was run and the two closest values were used. Ten percent of samples were run in triplicate. The correlation between best matching duplicates was 0.98 (R2=0.95) with a mean±SEM difference of 4.3±0.16 mV.

Statistical Analyses

Data was originally received in three data sets (data set 1 n=107; data set 2=197; data set 3=96). Data set 1 was used for all initial analyses. Data sets 2-3 were used as individual confirmation data sets. To control for differences in sperm numbers, sORP values were normed to the concentration of sperm in each sample. sORP values are presented as sORP/Concentration (mV/10$^6$ sperm/mL). For group comparisons, samples were grouped into "normal" or "abnormal" for each parameter based on the WHO reference for a normal parameter. In addition, only samples with a concentration greater than 0.999×10$^6$ sperm/mL were used, as these lower concentration escalated the sORP/Concentration average and resulted in artificially significant results. Relationships between sORP and measures of sperm quality were determined using Student's t-tests for group differences. A receiver operating characteristic (ROC) analysis was used to identify an sORP criterion that best predicts the abnormal morphology from normal, as defined by WHO criteria for sperm morphology. In this analysis, all data points were used regardless of sperm concentration. Significance was established at p<0.05. Graphs represent the mean+SEM.

The results show that there were no significant differences between the three data sets in reference to participant demographics, hormone levels, or semen parameters, confirming that all data sets are comparable to each other. Descriptive statistics for all data sets combined are shown in Table 3 below.

TABLE 3

Demographics and Descriptive Statistics of Study Participants

| | N | Mean | StDev | Median (IQR) |
|---|---|---|---|---|
| Age | 400 | 35.76 | 7.88 | 34 (9) |
| BMI | 352 | 31.62 | 26.99 | 27.85 (5.94) |
| Abstinence (days) | 400 | 4.35 | 2.21 | 4 (2) |
| Volume (mL) | 400 | 3.10 | 1.48 | 3.0 (2.0) |
| Total Cell # (×10$^6$) | 400 | 101.81 | 104.65 | 75.5 (130.75) |

TABLE 3-continued

Demographics and Descriptive Statistics of Study Participants

|  | N | Mean | StDev | Median (IQR) |
|---|---|---|---|---|
| Concentration ($10^6$ sperm/mL) | 400 | 33.33 | 30.13 | 28.0 (42.0) |
| Progressive Motility (%) | 400 | 14.08 | 14.32 | 10.0 (25.5) |
| Non-Progressive Motility (%) | 400 | 28.82 | 14.62 | 30.0 (19.0) |
| Non-Motile (%) | 400 | 57.11 | 23.54 | 52.5 (38.0) |
| Total Motility (%) | 400 | 42.90 | 23.59 | 47.5 (38.0) |
| Normal Morphology (%) | 400 | 7.00 | 8.44 | 4.00 (9.00) |
| sORP | 400 | 51.65 | 21.95 | 49.33 (26.0) |
| sORP/$10^6$ sperm/mL (sORP/Concentration) | 400 | 24.06 | 82.51 | 1.90 (4.9) |
| sORP/million cells (ORP/Cells)-Concentration > 0.999 M/mL | 366 | 4.54 | 8.20 | 1.64 (8.20) |
| Hormone Tests |  |  |  |  |
| Estradiol (E2) | 154 | 182.58 | 76.09 | 101.0 (52.0) |
| Luteinizing hormone (LH) | 243 | 4.41 | 2.71 | 4.0 (2.73) |
| Follicle stimulating horm (FSH) | 241 | 6.15 | 17.83 | 3.02 (4.0) |
| Protactin (PRL) | 242 | 235.15 | 175.67 | 195.0 (129.0) |
| Testosterone | 248 | 31.62 | 219.16 | 16.34 (9.80) |

Figure 17:
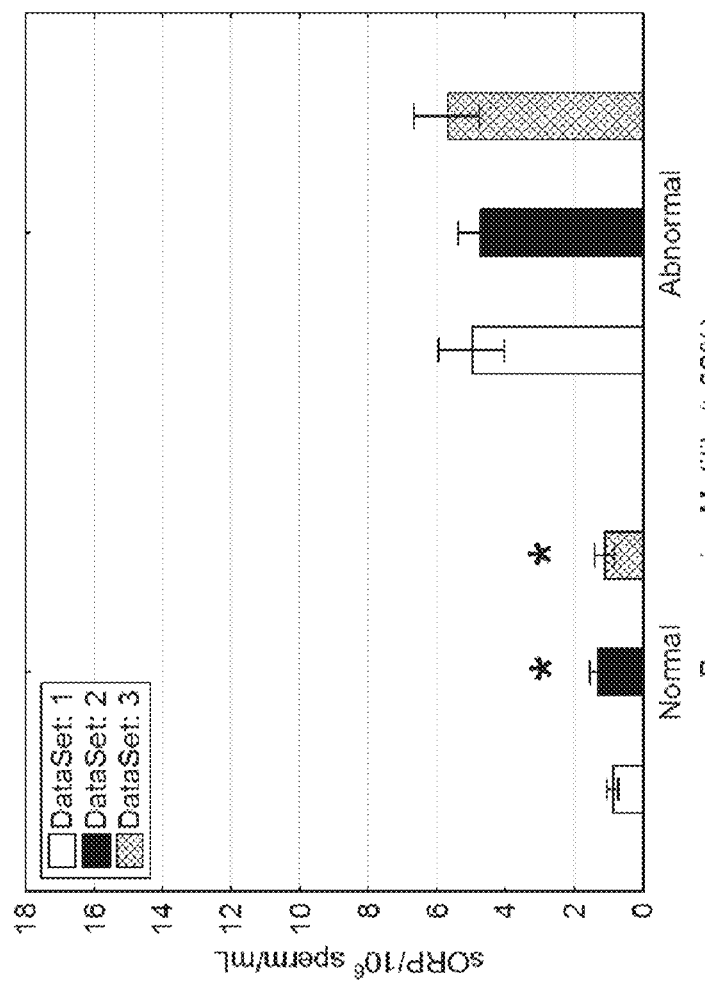
FIG. 17 shows a comparison of sORP/Conc. values from samples having a normal percent of progressively motile sperm (>32%) and samples having an abnormal progressive motility.
Figure 18:
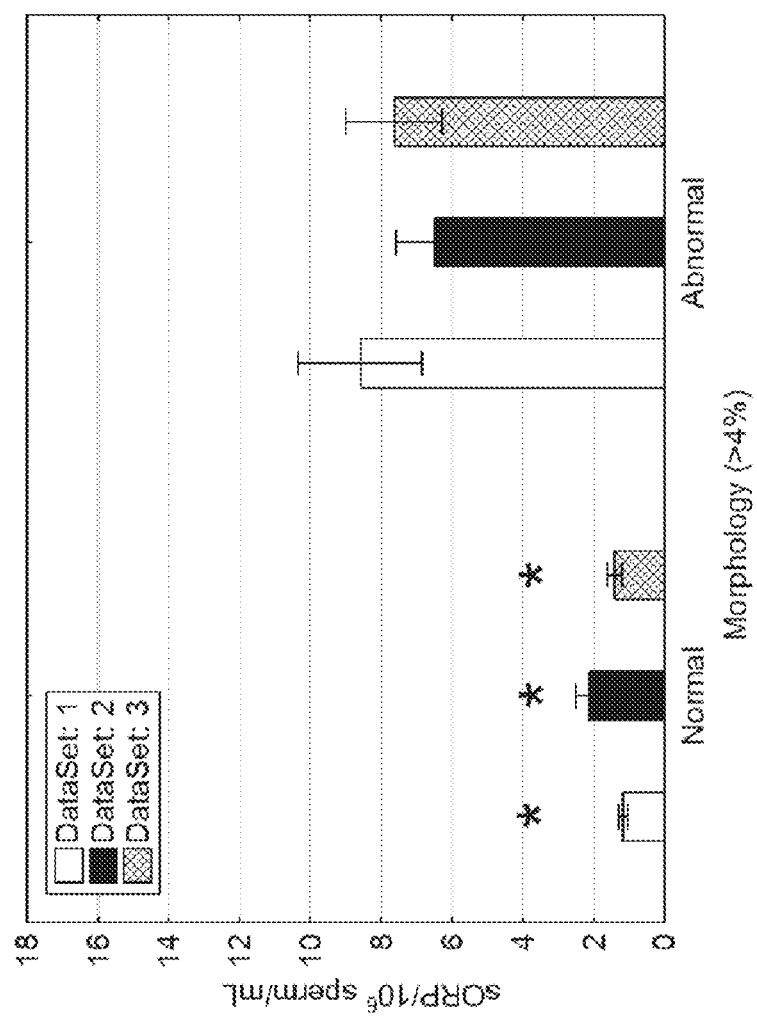
FIG. 18 shows a comparison of sORP/Conc. values from samples having a normal percent of sperm with healthy morphology (>4%) and samples having abnormal sperm cell morphology.

Based on analyses of data set 1, there were significant differences between normal and abnormal semen parameters (FIG. 13-18). Significantly higher sORP values were measured in samples that were abnormal compared to those that were normal in total cell number (t(98)=7.64, p<0.05) (FIG. 14), concentration (t(98)=7.74, p<0.05) (FIG. 15), total motility (t(98)=3.52, p<0.05) (FIG. 16), and morphology (t(98)=4.43, p<0.05) (FIG. 18). There was no significant differences found in semen volume (t(98)=1.24, p>0.05) (FIG. 13) or the percent of progressively motile sperm (t(98)=1.08, p>0.05) (FIG. 17). The differences in total cell number (FIG. 14), concentration (FIG. 15), total motility (FIG. 16), and morphology (FIG. 18) were confirmed in data sets 2 and 3 (p<0.05 for all). In addition, sORP as a function of progressive motility (FIG. 17) emerged as a significant effect in both remaining data sets (p<0.05). Volume continued to be insignificant.

A ROC analysis was used to determine if sORP could reliably be used to predict samples with abnormal morphology, thus emphasizing a high specificity and positive predictive value (PPV). Based on data set 1, an sORP/Concentration cut off value was identified at 3.29 mV/$10^6$ sperm/mL. A significant proportion of the area under the curve (AUC) was accounted for by sORP values (AUC=0.90 (95% CI 0.83-0.95), p<0.05). At the cut off value 3.29 mV/$10^6$ sperm/mL, specificity was 96.2% (95% CI 86.8-99.5) and a PPV of 94.1% (95% CI 80.3-99.3). Thus 96.2% of abnormal morphology samples were correctly identified and semen with sORP values greater than 3.29 mV/Concentration can be labeled as abnormal with 94.1% assurance. As shown in Table 4 below, this cut off value was confirmed using data sets 2 and 3, although with slightly lower predictive values.

TABLE 4

Summary of ROC Analysis For Predicting Sperm Morphology from sORP Values

| ORP Cut-Off = 3.29 mV | Data Set 1 | Data Set 2 | Data Set 3 | Combined Data Sets |
|---|---|---|---|---|
| AUC (*significant) | 0.90* | 0.77* | 0.83* | 0.82* |
| Sensitivity | 58.2 | 51.0 | 62.5 | 55.6 |
| Specificity | 96.2 | 87.0 | 85.0 | 89.1 |
| PPV | 94.1 | 82.1 | 83.0 | 85.7 |
| NPV | 68.5 | 60.2 | 65.9 | 63.1 |
| Accuracy | 77% | 68% | 72% | 71% |

Figure 13:
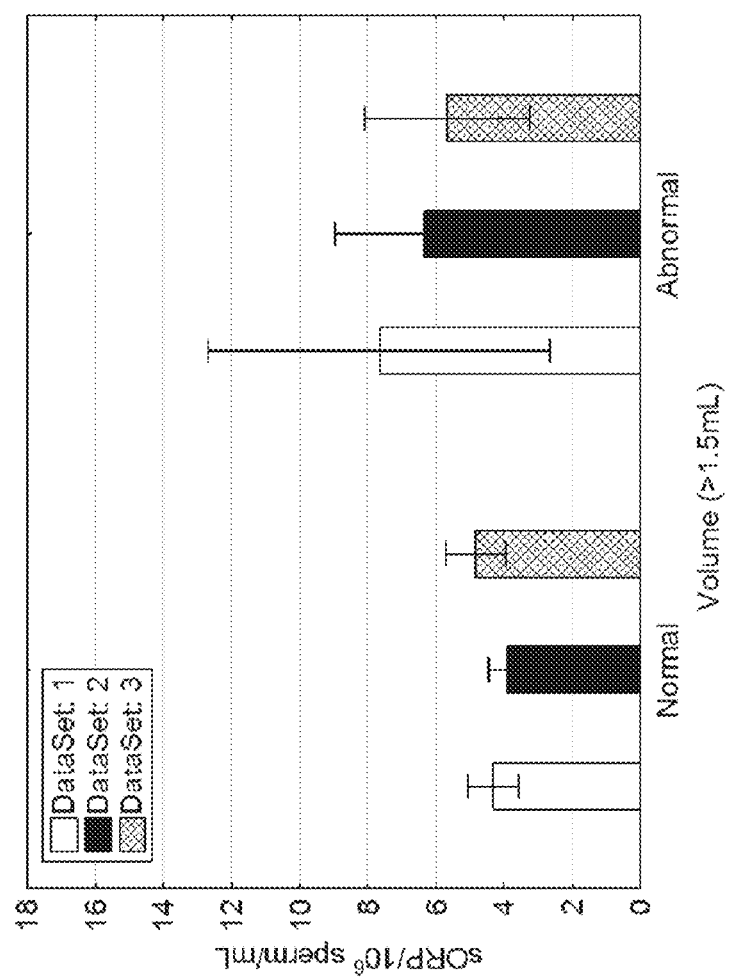
FIG. 13 shows a comparison of sORP/Conc. values from samples having normal ejaculate volume (>1.5 mL) and samples having an abnormal volume.
Figure 14:
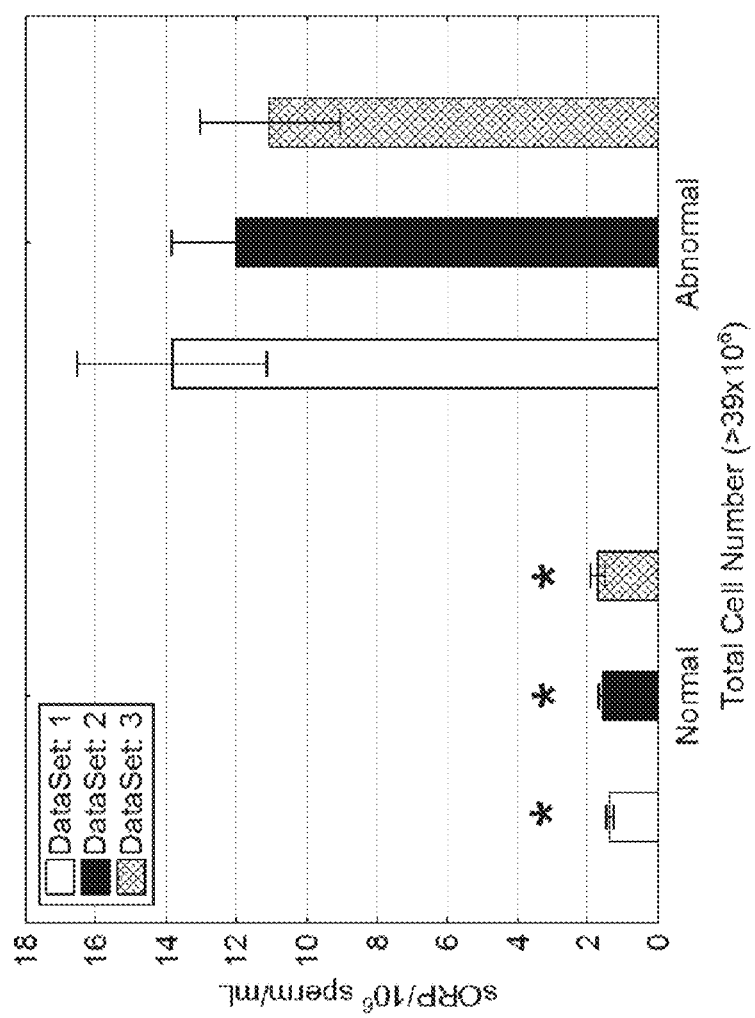
FIG. 14 shows a comparison of sORP/Conc. values from samples having normal sperm cell numbers ($>39 \times 10^6$ sperm) and samples having abnormal sperm cell numbers.
Figure 15:
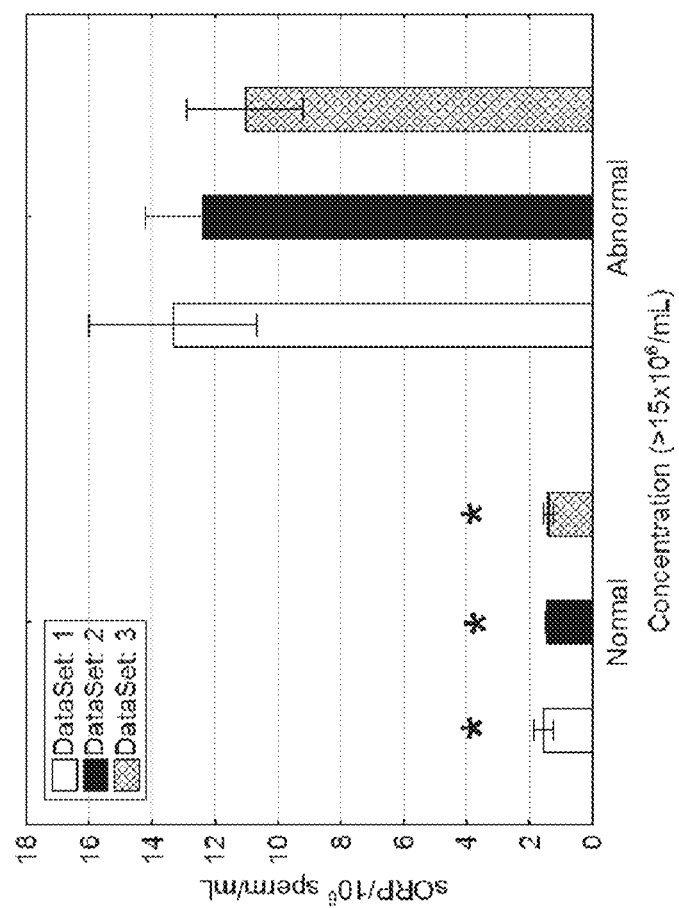
FIG. 15 shows a comparison of sORP/Conc. values from samples having normal sperm cell concentrations ($>15 \times 10^6$ sperm/mL) and samples having an abnormal sperm cell concentrations.
Figure 16:
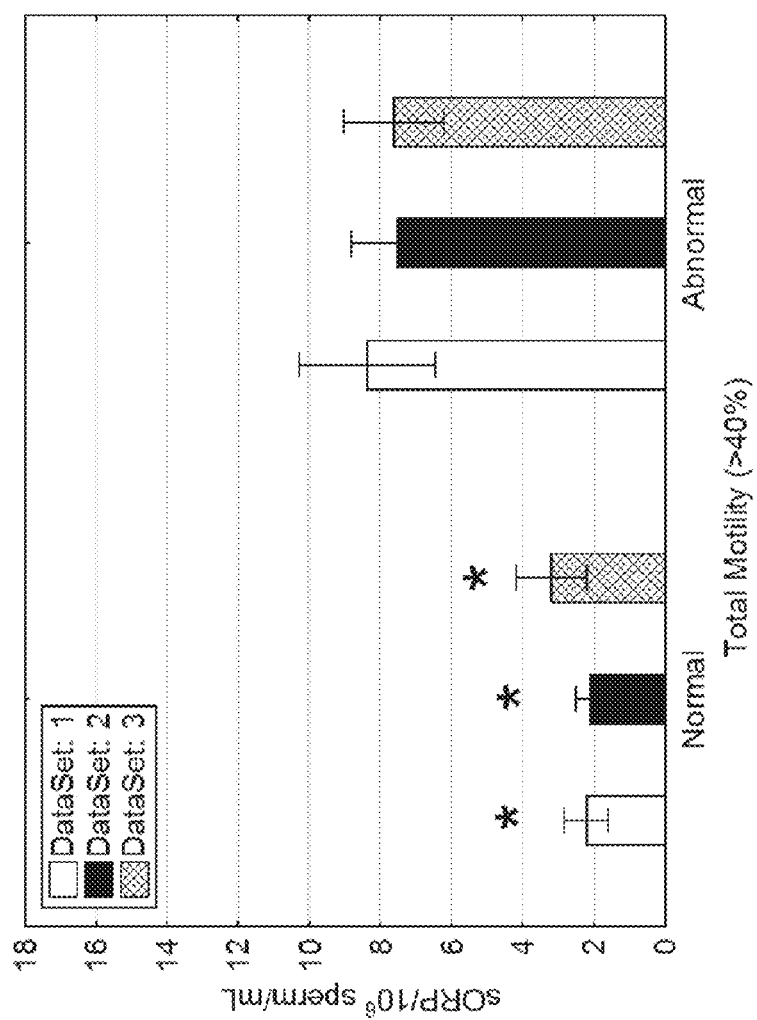
FIG. 16 shows a comparison of sORP/Conc. values from samples having a normal percent of total motile sperm (>40%) and samples having an abnormal sperm cell motility.
Figure 19:
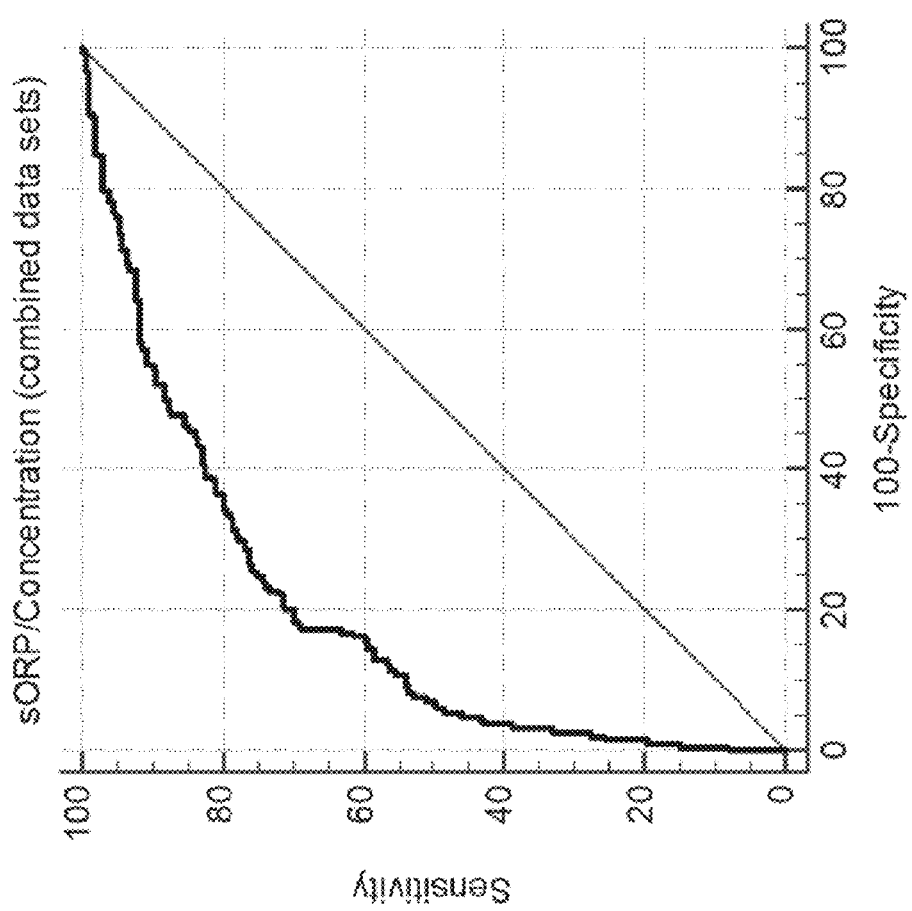
FIG. 19 ROC analysis for assessing the predictability of sperm morphology based on sORP values. Curved line represents the sORP values associated with various levels of sensitivity (y-axis) and specificity (x-axis) for distinguishing sperm morphology. Solid straight line represents the predictive ability based on statistical chance. The area between the two lines represents the area under the curve (AUC).

Combining all three data sets, specificity was 89.1% and PPV was 85.7%. FIG. 13 illustrates the ROC analysis graph showing the area under the curve. The AUC in FIG. 19 was significant (p<0.05), indicating the predictive ability of sORP value is significantly greater than chance.

The results show that sORP values were significantly higher in samples having abnormal semen parameters. The results also demonstrate that an sORP cut-off value of 3.29 mV/$10^6$ sperm/ml, determined from Data Set 1, accurately identified 96.2% of all samples having normal morphology. Thus, a sample having an sORP/Concentration greater than 3.29 has an 85.7% chance of having abnormal sperm morphology.

What is claimed:

1. A method of evaluating the fertility potential of a successful implantation of a fertilized egg, comprising:
    a. measuring the static oxidation-reduction potential (sORP) and/or the capacity oxidation-reduction potential (cORP) of medium in which a fertilized egg is being cultured;
    b. comparing the measured sORP and/or cORP of a sample of the medium to a reference value, wherein if the ORP value of the medium being tested is significantly increased compared to the reference value, the fertilized egg cultured in the medium is identified as being unlikely to establish and maintain a successful implantation; and
    c. treating the medium with an antioxidant if the ORP value of the medium being tested is significantly increased compared to the reference value.

2. The method of claim 1, wherein the fertilized egg being cultured is a zygote.

3. The method of claim 1, wherein the fertilized egg being culture is a blastocyst.

4. The method of claim 1, wherein the medium is compared every 30 minutes, 1 hour, 2 hours, 3 hours, 4 hours, 5 hours, 6 hours, 12 hours or 18 hours.

5. The method of claim 1, wherein the medium is compared every 1 day, 2 days or every 3 days.

6. The method of claim 1, wherein the reference value is determined from the sORP and/or cORP level in follicular fluid of oocytes.

7. The method of claim 1, wherein the antioxidant is ascorbic acid.

8. A method of improving the likelihood that a fertilized egg will achieve a successful pregnancy, comprising:
   a. measuring the static oxidation-reduction potential (sORP) and/or the capacity oxidation-reduction potential (cORP) of medium in which a fertilized egg is being cultured;
   b. comparing the measured sORP and/or cORP of a sample of the medium to a reference value, wherein if the ORP value of the medium being tested is significantly increased compared to the reference value, the fertilized egg cultured in the medium is identified as being unlikely to establish and maintain a successful implantation;
   c. treating the medium with an antioxidant if the ORP value of the sample being tested is significantly increased compared to the reference value;
   d. comparing a sample of the treated medium of step (c) to the reference value;
   e. identifying the fertilized egg cultured in the medium as likely to establish and maintain a successful implantation if the ORP value of the treated medium sample is about the same as the reference value; and
   f. implanting the fertilized egg.

9. The method of claim 8, wherein the fertilized egg being cultured is a zygote.

10. The method of claim 8, wherein the fertilized egg being culture is a blastocyst.

11. The method of claim 8, wherein the medium is compared every 30 minutes, 1 hour, 2 hours, 3 hours, 4 hours, 5 hours, 6 hours, 12 hours or 18 hours.

12. The method of claim 8, wherein the medium is compared every 1 day, 2 days or every 3 days.

13. The method of claim 8, wherein the reference value is determined from the sORP and/or cORP level in follicular fluid of oocytes.

14. The method of claim 8, wherein the antioxidant is ascorbic acid.

* * * * *